(12) United States Patent
Griffin

(10) Patent No.: US 9,610,126 B2
(45) Date of Patent: Apr. 4, 2017

(54) FLEXIBLE CONTAINERS FOR USE IN STERILIZING, STORING, TRANSPORTING, AND PRESENTING MEDICAL INSTRUMENTS

(71) Applicant: Practicon, Inc., Greenville, NC (US)

(72) Inventor: Bradley P. Griffin, Greenville, NC (US)

(73) Assignee: Practicon, Inc., Greenville, NC (US)

( * ) Notice: Subject to any disclaimer, the term of this patent is extended or adjusted under 35 U.S.C. 154(b) by 0 days.

(21) Appl. No.: 14/281,218

(22) Filed: May 19, 2014

(65) Prior Publication Data

US 2014/0339114 A1 Nov. 20, 2014

Related U.S. Application Data

(60) Provisional application No. 61/825,128, filed on May 20, 2013.

(51) Int. Cl.

| | | |
|---|---|---|
| *A61B 19/02* | (2006.01) | |
| *A61B 50/20* | (2016.01) | |
| *A61B 50/30* | (2016.01) | |
| *A61L 2/07* | (2006.01) | |
| *A61L 2/18* | (2006.01) | |
| *A61L 2/20* | (2006.01) | |
| *A61B 50/00* | (2016.01) | |

(52) U.S. Cl.
CPC .............. *A61B 19/02* (2013.01); *A61B 50/00* (2016.02); *A61B 50/20* (2016.02); *A61B 50/30* (2016.02); *A61B 2050/006* (2016.02); *A61B 2050/0083* (2016.02); *A61L 2/07* (2013.01); *A61L 2/18* (2013.01); *A61L 2/20* (2013.01); *A61L 2202/24* (2013.01)

(58) Field of Classification Search
CPC ........ A61L 2/00; A61L 2/26; A61L 2202/182; A61L 2202/24; A61L 2/07; A61L 2/18; A61B 19/02; A61B 50/00; A61B 50/20; A61B 50/30; A61B 2050/006; A61B 2050/0083
USPC ..... 206/363, 370, 371, 438, 508; 220/573.1, 220/219, DIG. 6
See application file for complete search history.

(56) References Cited

U.S. PATENT DOCUMENTS

| | | | | |
|---|---|---|---|---|
| 4,798,292 | A * | 1/1989 | Hauze ........................... | 206/439 |
| 5,279,800 | A * | 1/1994 | Berry, Jr. ...................... | 422/300 |
| 6,116,452 | A * | 9/2000 | Hamel et al. ................. | 220/318 |
| 6,264,902 | B1 | 7/2001 | Howlett | |
| 6,365,115 | B1 | 4/2002 | Wood | |
| 6,379,631 | B1 | 4/2002 | Wu | |

(Continued)

FOREIGN PATENT DOCUMENTS

| | | |
|---|---|---|
| EP | 0750517 A1 | 1/1997 |
| EP | 1053755 A2 | 11/2000 |
| EP | 0804253 B1 | 8/2001 |

*Primary Examiner* — Chun Cheung
(74) *Attorney, Agent, or Firm* — Ward and Smith, P.A.; Ryan K. Simmons

(57) ABSTRACT

Instrument containers for use in sterilizing, storing, transporting, and/or presenting medical instruments, such as dental and surgical instruments, are disclosed. The instrument containers may include, an instrument tray; a cover; and a plurality of openings formed in the instrument tray and cover. The instrument containers may be flexible containers, wherein the cover can be snap-fitted onto the instrument tray.

17 Claims, 23 Drawing Sheets

(56) References Cited

U.S. PATENT DOCUMENTS

| | | |
|---|---|---|
| 6,572,819 B1 | 6/2003 | Wu et al. |
| 6,692,693 B2 | 2/2004 | Wu |
| 7,021,485 B1* | 4/2006 | Baker et al. ................. 220/326 |
| 8,272,508 B2* | 9/2012 | Bettenhausen et al. ...... 206/370 |
| 2005/0095169 A1 | 5/2005 | Su-Syin |
| 2007/0104609 A1* | 5/2007 | Powell ............................. 422/1 |
| 2008/0159918 A1 | 7/2008 | Wu |
| 2011/0071572 A1* | 3/2011 | Sixto et al. .................. 606/286 |

* cited by examiner

# FLEXIBLE CONTAINERS FOR USE IN STERILIZING, STORING, TRANSPORTING, AND PRESENTING MEDICAL INSTRUMENTS

CROSS REFERENCE TO RELATED APPLICATION

This application is related to and claims priority to U.S. Provisional Patent Application Ser. No. 61/825,128, filed May 20, 2013. The disclosure of the referenced Provisional application is specifically incorporated by reference herein.

TECHNICAL FIELD

The present invention relates generally to containers for handling medical instruments and more particularly to flexible containers for use in sterilizing, storing, transporting, and presenting medical instruments, such as dental and surgical instruments.

BACKGROUND

Containers that are used for sterilizing, storing, transporting, and presenting medical instruments, such as dental and surgical instruments, are typically formed of hard, rigid materials, such as stainless steel or aluminum. Additionally, conventional instrument containers include moving parts, such as hinges and latches. However, there are numerous drawbacks to these instrument containers. Examples of drawbacks include, but are not limited to, (1) metal instrument containers require a cool down period after heat sterilization before handling to avoid the risk of burning the user's hands; (2) metal instrument containers may have sharp edges and corners, which may tear latex gloves and/or injure the user's hands; (3) metal instrument containers can be noisy due to metal-to-metal contact of the container with the metal instruments therein; (4) the metal surfaces of metal instrument containers tend to rub or scratch against the instruments therein, thus there is a risk of damage to the instruments therein; (5) metal instrument containers are not well-suited for use within a limited workspace; namely, metal instrument containers often include a hinged cover that opens 180 degrees, thus making the footprint of the opened container twice that of the closed container; (6) metal instrument containers include moving parts, such as hinges, latches, and the like, that can break or wear out over time; and (7) metal instrument containers can be expensive. Therefore, new approaches are needed to overcome the aforementioned drawbacks of conventional instrument containers for sterilizing, storing, transporting, and presenting medical instruments, such as dental and surgical instruments.

BRIEF DESCRIPTION OF THE DRAWINGS

The features and advantages of the present invention will be more clearly understood from the following description taken in conjunction with the accompanying drawings, wherein.

DETAILED DESCRIPTION

Figure 1:
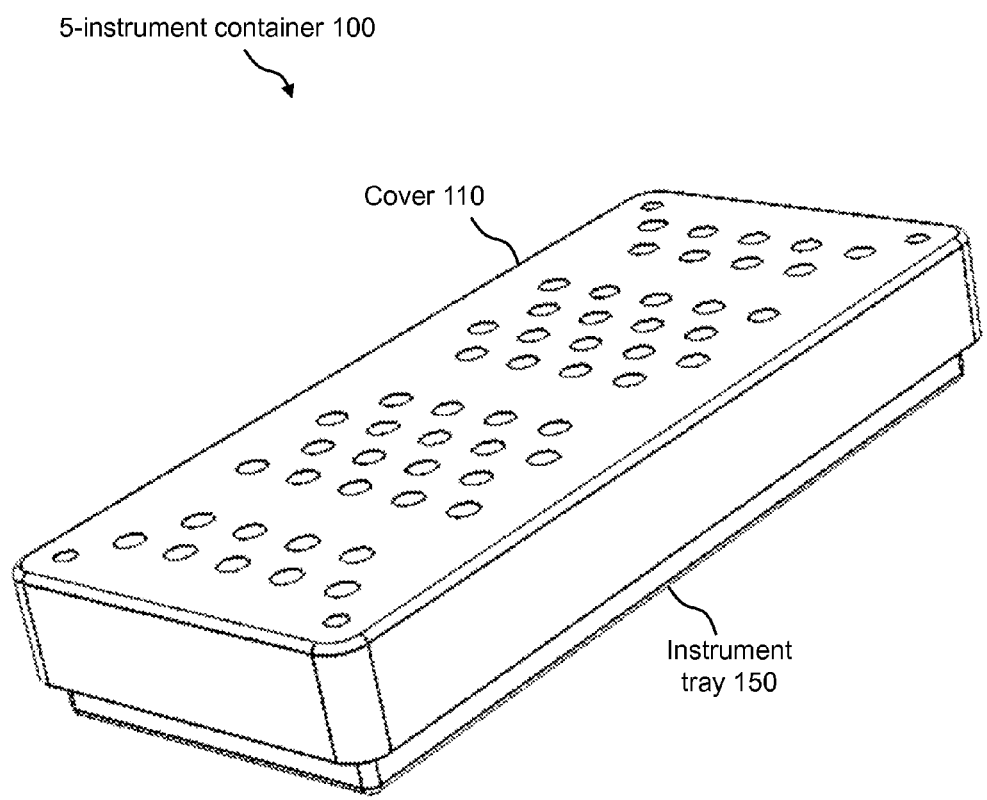
FIG. 1 illustrates a perspective view of a 5-instrument container, which is one example of a flexible container for use in sterilizing, storing, transporting, and presenting medical instruments.

Flexible containers for use in sterilizing, storing, transporting, and presenting medical instruments, such as dental and surgical instruments, are provided. In one example, a 5-instrument flexible container is provided. In another example, a 10-instrument flexible container is provided. In yet another example, a 14-instrument flexible container is provided. Each of the flexible containers includes an instrument tray and a cover that can be formed by, for example, an injection molding process.

Features of the instrument tray include, but are not limited to:

(1) Openings to promote the circulation of air, sterilization vapors, and liquids. Typically, the openings substantially align with openings in the cover so as to maximize flow of these agents. Further, the interior edges of the openings are typically rounded to break surface tension of liquids that may be pooled on the inside surfaces of the instrument tray, thereby improving drainage;

(2) Instrument rests that hold a number of dental and/or surgical instruments in parallel position and in close proximity to each other;

(3) Customizable instrument rests, wherein the silicone construction (as an example) allows the instrument rests to be cut with scissors to accommodate large handled instruments;

(4) One or more pairs of flexible clips to securely retain, for example, one or more air/water syringe tips during storage and processing;

(5) Detent features of a ball-and-detent corner-lock system that receives corresponding ball features in the cover, wherein the ball-and-detent corner-lock system allows the cover to be snap-fitted onto the instrument tray; and (6) Raised ball feet at the corners that substantially align with corresponding detents on the cover so as to aid in alignment and stability when stacking multiple flexible containers.

Features of the cover include, but are not limited to:

(1) Openings to promote the circulation of air, sterilization vapors, and liquids. Typically, the openings substantially align with openings in the instrument tray so as to maximize flow of these agents. Further, the interior edges of the openings are typically rounded to break surface tension of liquids that may be pooled on the inside surfaces of the cover, thereby improving drainage;

(2) Perimeter drainage channels that create a passageway for liquids to drain rapidly from the interior of the flexible container when the closed container is stored on its side;

(3) Instrument retention fingers that are sized and positioned to bend and flex around variously sized instrument handles so that the fingers retain instruments within the instrument rests in the instrument tray;

(4) Ball features of the ball-and-detent corner-lock system that keeps the cover retained upon the instrument tray when pressed closed; and (5) Detents at the corners that substantially align with corresponding raised ball feet on the instrument tray so as to aid in alignment and stability when stacking multiple flexible containers.

While a 5-instrument flexible container, a 10-instrument flexible container, and a 14-instrument flexible container are disclosed herein below, these are exemplary only. The flexible container disclosed herein is not limited to holding 5, 10, and 14 instruments only. The flexible container can be sized and designed to hold any number of instruments. Further, while the 5-instrument flexible container, the 10-instrument flexible container, and the 14-instrument flexible container disclosed herein below are designed for processing dental instruments, again this is exemplary only. The flexible container disclosed herein is not limited to holding dental instruments only. The flexible container can be sized and designed to hold any type of medical instruments, such as, but not limited to, dental and surgical instruments.

FIG. 1 illustrates a perspective view of a 5-instrument container 100, which is one example of a flexible container for use in sterilizing, storing, transporting, and presenting medical instruments. The 5-instrument container 100 is an example of a flexible container for holding five instruments, such as five dental instruments. FIG. 1 shows the 5-instrument container 100 in a closed state. The 5-instrument container 100 includes a cover 110 that can be snap-fitted onto an instrument tray 150. In this example, the features of the 5-instrument container 100 are designed and sized to hold five dental instruments in parallel position and in close proximity to each other. In addition to the five dental instruments held in parallel, the 5-instrument container 100 is designed and sized to hold, for example, an air/water syringe tip. Further, in this example, the overall geometry of the 5-instrument container 100 is box-shaped with a generally rectangular footprint.

Both cover 110 and instrument tray 150 (and any features thereof) are formed of a flexible material. For example, cover 110 and interment tray 150 (and any feature thereof) may be formed of silicone via a standard injection molding process, thereby forming a soft, flexible, pliable, 5-instrument container 100.

Figure 2:
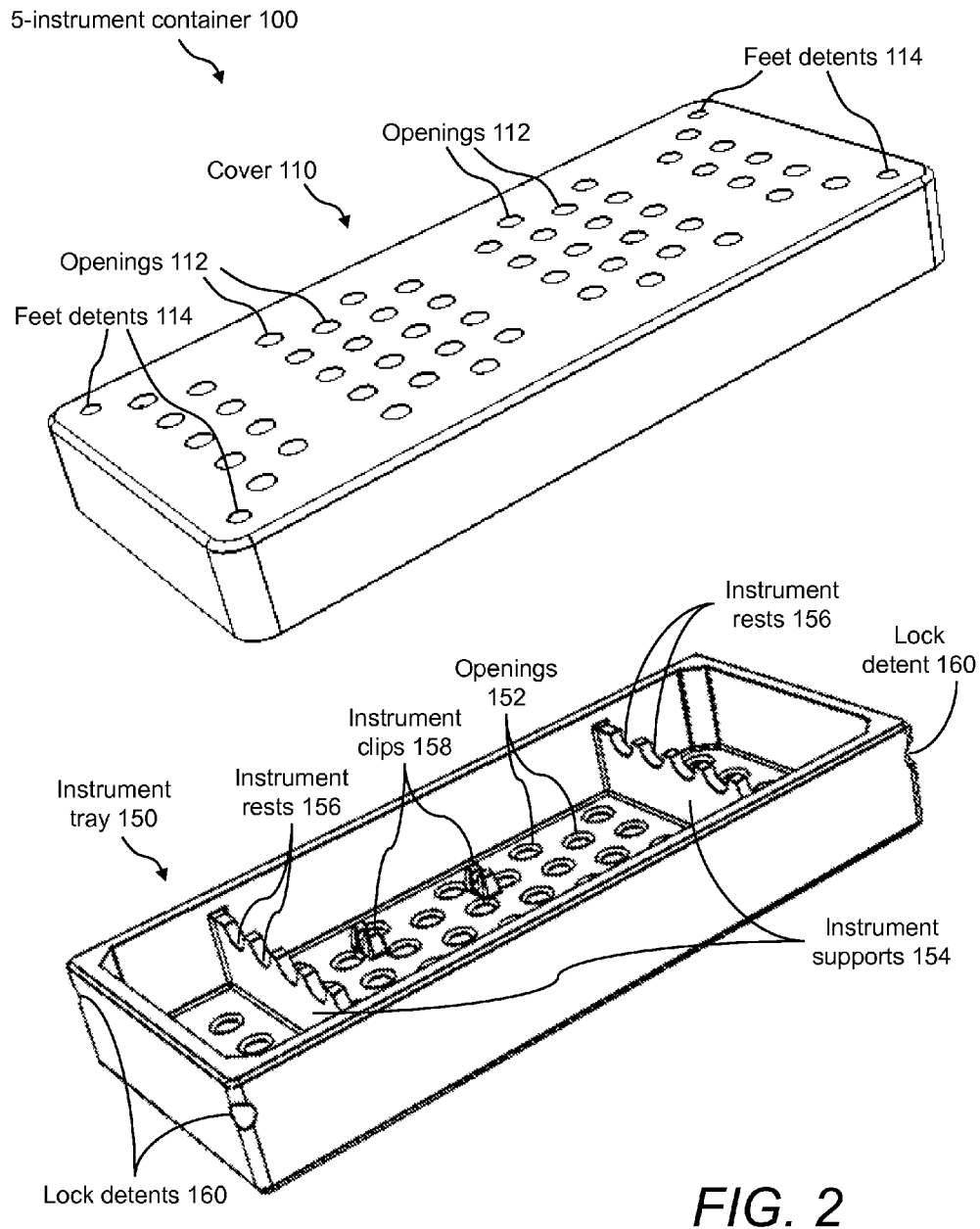
FIG. 2 illustrates a perspective view of a cover and an instrument tray of the 5-instrument container shown in FIG. 1.

FIG. 2 illustrates a perspective view of cover 110 and instrument tray 150 of the 5-instrument container 100 when separated (i.e., in an opened state) and showing certain details of both. Namely, FIG. 2 shows certain details of the outside of cover 110 and certain details of the inside and outside of instrument tray 150. For example, cover 110 includes an arrangement of openings 112 across the area thereof. For example, a plurality of openings 112 can be arranged in columns, rows, clusters, and/or any configurations. In the example shown in FIG. 1 and FIG. 2, cover 110 includes an arrangement of 54 openings 112, arranged as shown. Cover 110 also typically includes a set of feet detents 114. In one example, cover 110 includes four feet detents 114; one at each corner of cover 110, as shown. More details of cover 110 of the 5-instrument container 100 are shown and described with reference to FIG. 4 and FIG. 5.

Instrument tray 150 includes an arrangement of openings 152 across the area thereof. For example, a plurality of openings 152 can be arranged in columns, rows, clusters, and/or any configurations. In the example shown in FIG. 2, instrument tray 150 includes an arrangement of 54 openings 152, which substantially align with openings 112 of cover 110 when the 5-instrument container 100 is closed. When in use, openings 112 in cover 110 and openings 152 in instrument tray 150 allow the circulation of air, sterilization vapors, and liquids through the 5-instrument container 100. Instrument tray 150 also typically includes at least two instrument supports 154; namely, one instrument support 154 near one end of instrument tray 150 and another instrument support 154 near the other end of instrument tray 150. However, instrument tray 150 is not limited to two instrument supports 154 only. Each instrument support 154 includes a plurality of instrument rests 156, which are troughs or semicircular features that substantially conform to the geometry of certain instruments (not shown) to be held in the 5-instrument container 100. In the 5-instrument container 100 as shown, each instrument support 154 includes five instrument rests 156. Accordingly, the 5-instrument container 100 can hold five instruments, such as five dental instruments (not shown).

Additionally, instrument tray 150 typically includes a pair of instrument clips 158 to securely retain, for example, an air/water syringe tip (not shown) during storage and processing. Instrument clips 158 sit below the height of instrument supports 154 so that the air/water syringe tip does not interfere with instruments held atop instrument supports 154.

Instrument tray 150 also typically includes a set of lock detents 160. In one example, instrument tray 150 includes four lock detents 160; one at the outside of each corner of instrument tray 150, as shown. More details of instrument tray 150 of the 5-instrument container 100 are shown and described with reference to FIG. 6 and FIG. 7.

Figure 3:
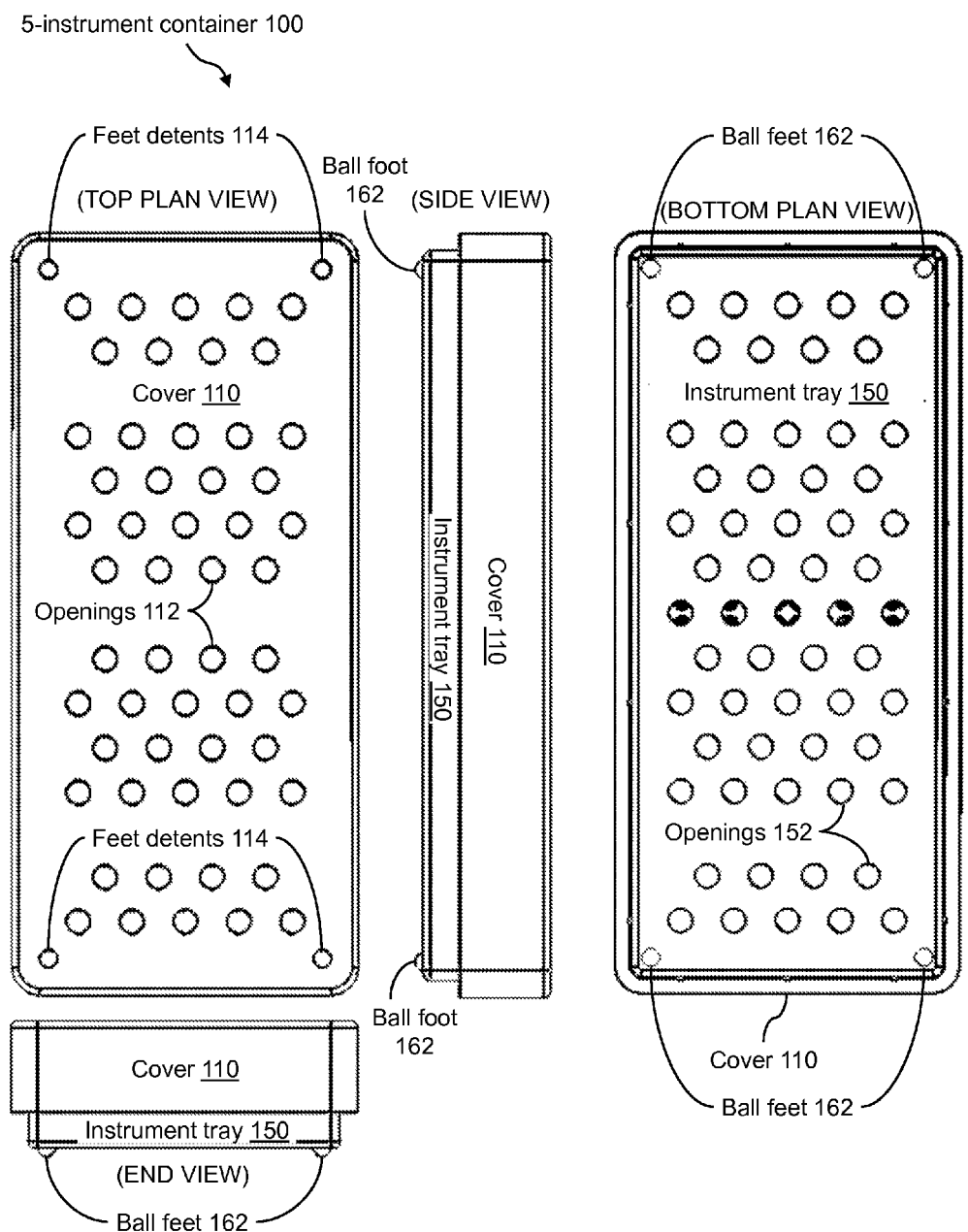
FIG. 3 illustrates a top plan view, a bottom plan view, a side view, and an end view of the 5-instrument container shown in FIG. 1.

FIG. 3 illustrates a top plan view, a bottom plan view, a side view, and an end view of the 5-instrument container 100 in the closed state. FIG. 3 shows that instrument tray 150 also includes a set of external ball feet 162. In one example, instrument tray 150 includes four ball feet 162; one at each corner of instrument tray 150, as shown in the bottom plan view.

Figure 4:
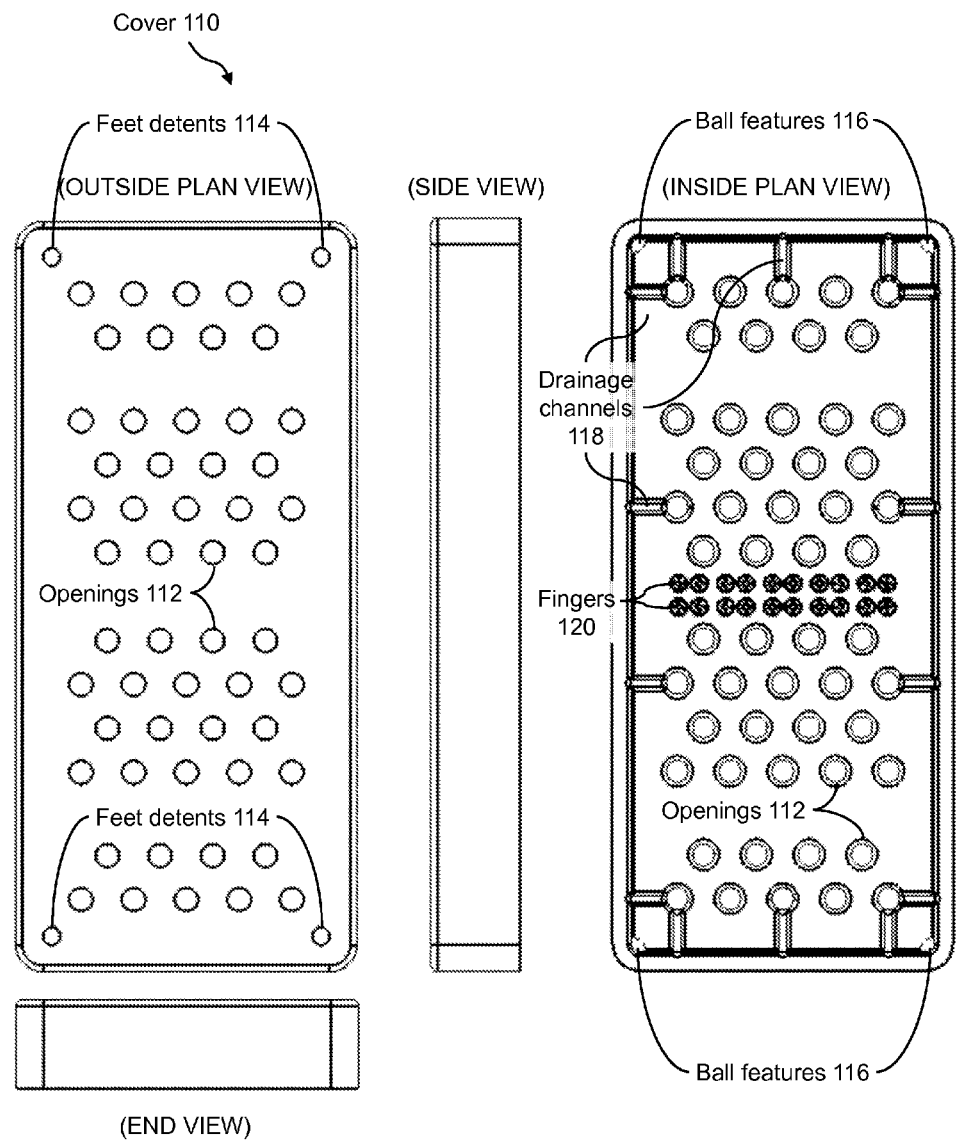
FIG. 4 illustrates an outside plan view, an inside plan view, a side view, and an end view of the cover of the 5-instrument container shown in FIG. 1.
Figure 5:
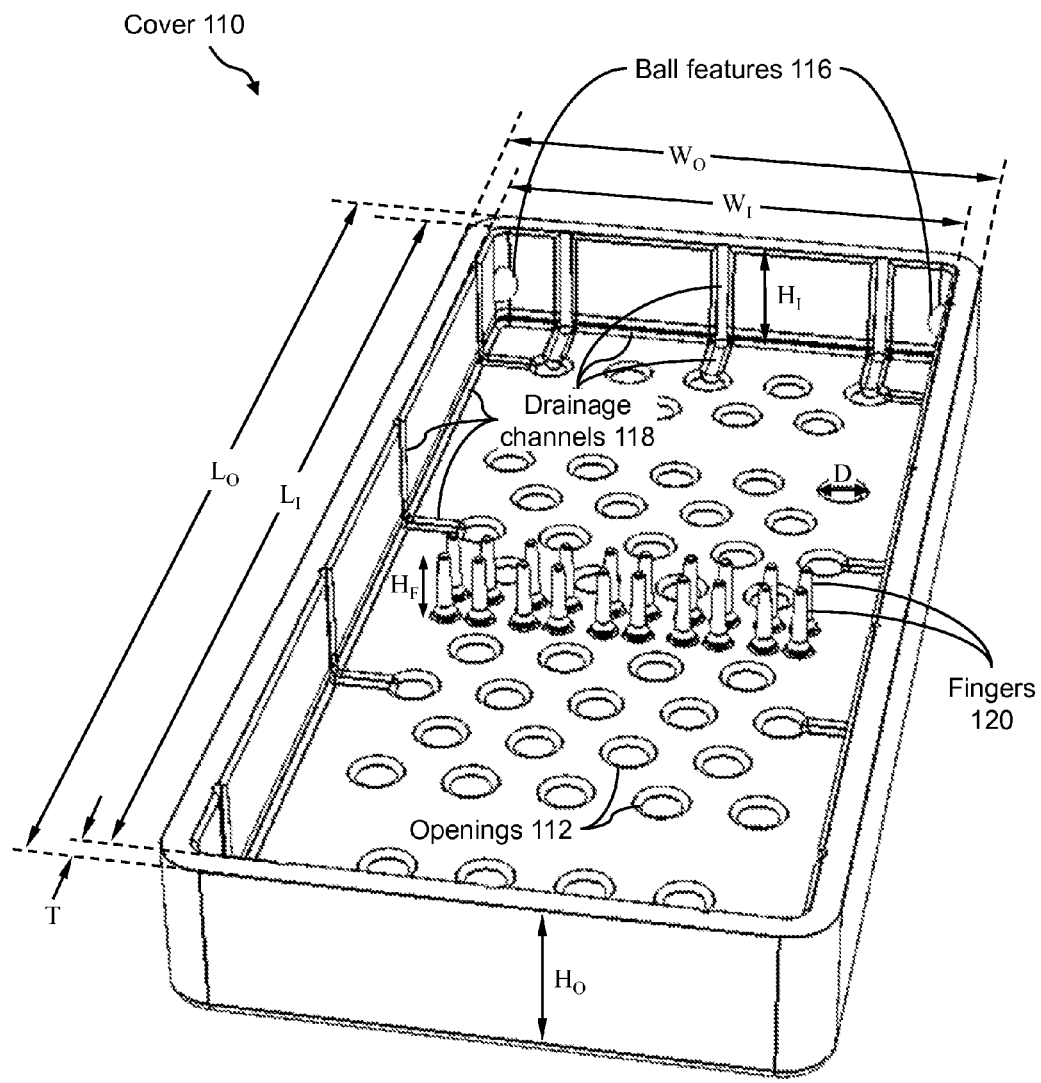
FIG. 5 illustrates a perspective view of the inside of the cover of the 5-instrument container shown in FIG. 1.

FIG. 4 illustrates an outside plan view, an inside plan view, a side view, and an end view of cover 110 of the 5-instrument container 100 shown in FIG. 1. FIG. 5 illustrates a perspective view of the inside of cover 110 of the 5-instrument container 100 shown in FIG. 1. FIG. 4 and FIG. 5 show openings 112 and feet detents 114 of cover 110. However, FIG. 4 and FIG. 5 show that the inside of cover 110 also includes a set of ball features 116. In one example, cover 110 includes four ball features 116; one at each corner of cover 110, as shown in the inside plan view of FIG. 4 and in FIG. 5. The combination of the four ball features 116 in cover 110 and the four lock detents 160 in instrument tray 150 (see FIG. 2, FIG. 6, and FIG. 7) forms a ball-and-detent corner-lock system in 5-instrument container 100. Namely, cover 110 is secured atop instrument tray 150 by pressing cover 110 onto instrument tray 150 and snap-fitting the four ball features 116 of cover 110 into the four lock detents 160 of instrument tray 150.

Further, the inside plan view of FIG. 4 and FIG. 5 show that cover 110 also includes a plurality of drainage channels 118 and a set of fingers 120. For example, cover 110 includes a drainage channel 118 around its perimeter as well as other drainage channels 118 leading from openings 112 at the perimeter of cover 110 to the perimeter drainage channel 118. Drainage channels 118 are provided to ensure adequate drainage of cleaning solutions out of the 5-instrument container 100 after immersion, washing, or sterilization as required. Namely, drainage channels 118 create a passageway for liquids to drain from the interior of the 5-instrument container 100 when the closed container is stored on its side. By their design, drainage channels 118 cannot be blocked in any way inadvertently.

Fingers 120 are instrument retention fingers. Fingers 120 are sized and positioned to bend and flex around variously sized instruments (not shown) within the 5-instrument container 100. Namely, when the 5-instrument container 100 is closed, fingers 120 of cover 110 press against any instruments within instrument rests 156 of instrument tray 150, thereby retaining the instruments within instrument rests 156.

Cover 110 of the 5-instrument container 100 has certain dimensions, as shown in FIG. 5. For example, cover 110 has an inside length $L_I$, an inside width $W_I$, and an inside height $H_I$. Further, cover 110 has an outside length $L_O$, an outside width $W_O$, and an outside height $H_O$. The material forming the walls and floor of cover 110 has a thickness T. Additionally, fingers 120 have a height $H_F$ and openings 112 have a diameter D. The inside length $L_I$, inside width $W_I$, and inside height $H_I$ are set so that cover 110 can be fitted upon instrument tray 150. Examples of dimensions of cover 110 of the 5-instrument container 100 are shown in Table 1 below.

TABLE 1

Example dimensions of cover 110 of the 5-instrument container 100

| Dimension | Tolerance (inches) | Specific Example (inches) |
|---|---|---|
| Inside length $L_I$ | +0.125/−0.0 | about 7.623 |
| Inside width $W_I$ | +0.125/−0.0 | about 3.248 |
| Inside height $H_I$ | +0.125/−0.0 | about 0.750 |
| Thickness T | +0.063/−0.0 | about 0.188 |
| Outside length $L_O$ | +0.125/−0.0 | about 8.000 |
| Outside width $W_O$ | +0.125/−0.0 | about 3.625 |
| Outside height $H_O$ | +0.125/−0.0 | about 0.938 |
| Height $H_F$ | +0.063/−0.0 | about 0.438 |
| Diameter D | +0.063/−0.0 | about 0.250 |

Figure 6:
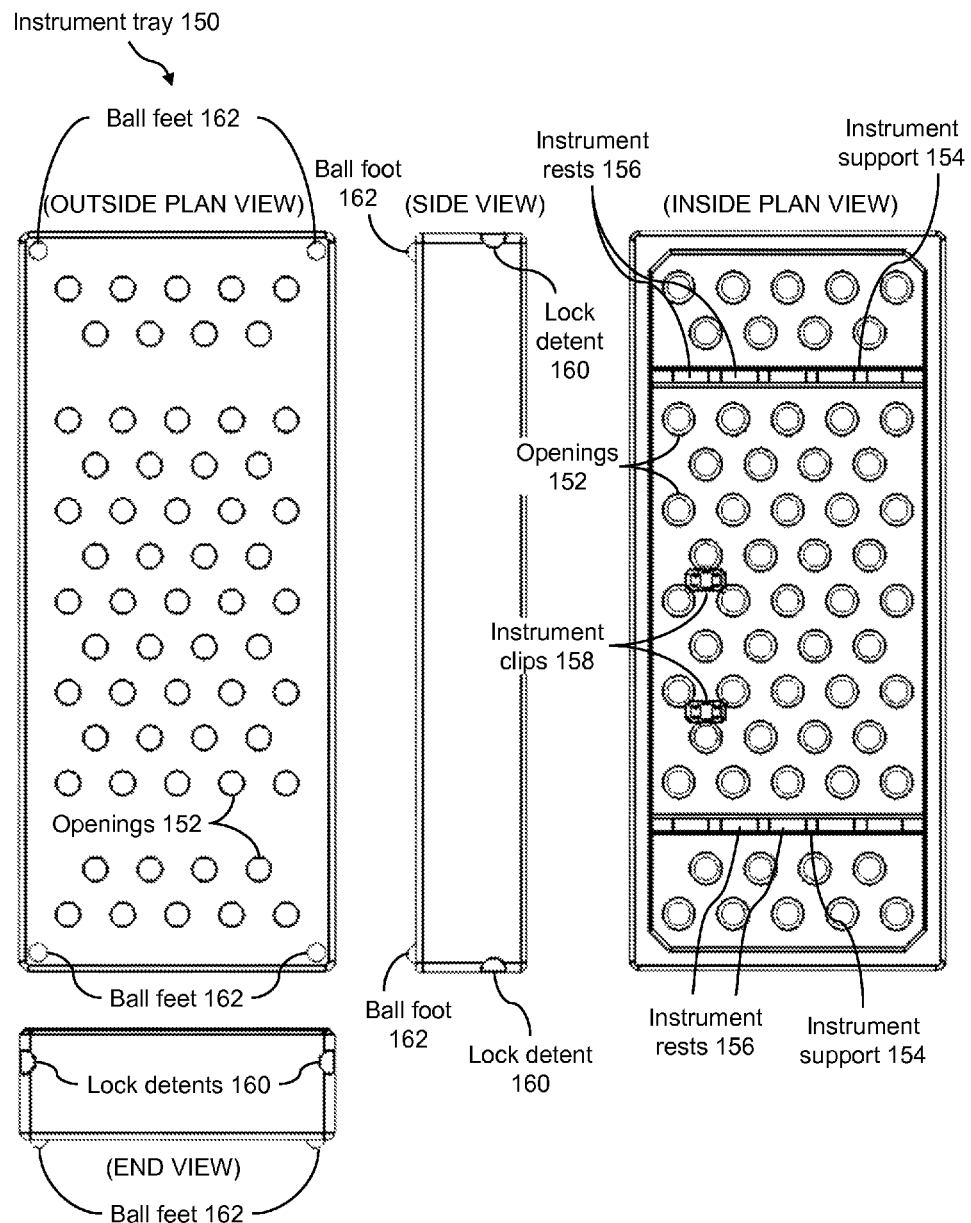
FIG. 6 illustrates an outside plan view, an inside plan view, a side view, and an end view of the instrument tray of the 5-instrument container shown in FIG. 1.
Figure 7:
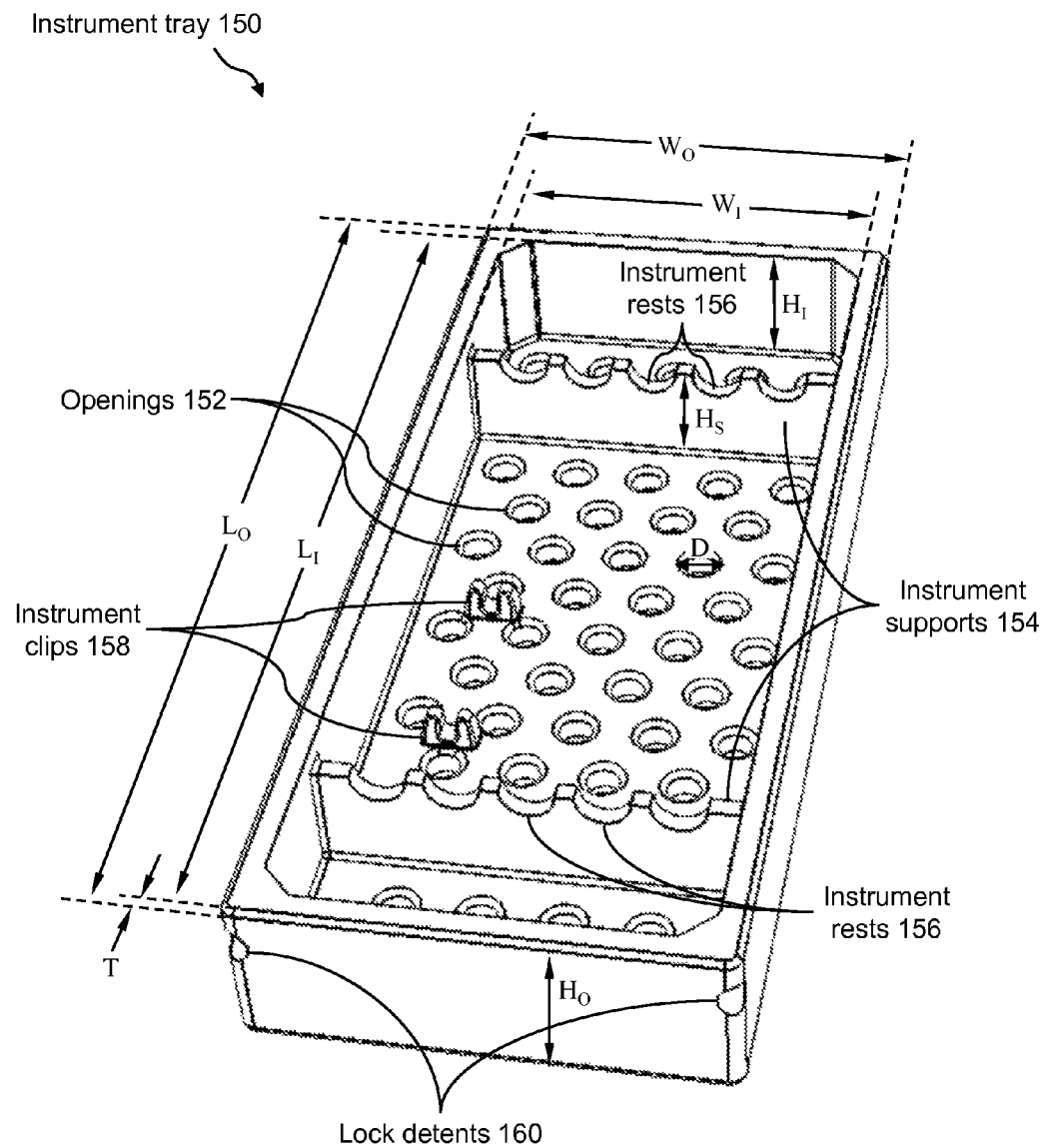
FIG. 7 illustrates a perspective view of the inside of the instrument tray of the 5-instrument container shown in FIG. 1.

FIG. 6 illustrates an outside plan view, an inside plan view, a side view, and an end view of instrument tray 150 of the 5-instrument container 100 shown in FIG. 1. FIG. 7 illustrates a perspective view of the inside of instrument tray 150 of the 5-instrument container 100 shown in FIG. 1. FIG. 6 and FIG. 7 show openings 152, instrument supports 154 that include instrument rests 156, instrument clips 158, lock detents 160, and ball feet 162 of instrument tray 150. Note that the locations and number of ball feet 162 of instrument tray 150 substantially correspond to the locations and number of feet detents 114 of cover 110. Namely, feet detents 114 of cover 110 are designed to receive ball feet 162 of instrument tray 150 so that a first 5-instrument container 100 can be stacked upon a second 5-instrument container 100. In fact, any number of 5-instrument containers 100 can be stacked, while feet detents 114 of each cover 110 and ball feet 162 of each instrument tray 150 assist in keeping the stack orderly and stable.

Instrument tray 150 of the 5-instrument container 100 has certain dimensions, as shown in FIG. 7. For example, instrument tray 150 has an inside length $L_I$, an inside width $W_I$, and an inside height $H_I$. Further, instrument tray 150 has an outside length $L_O$, an outside width $W_O$, and an outside height $H_O$. The material forming the walls and floor of instrument tray 150 has a thickness T. Additionally, instrument supports 154 have a height $H_S$ and openings 152 have a diameter D. The inside length $L_I$, inside width $W_I$, and inside height $H_I$ are set according to the size of the instruments to be held in instrument tray 150. Examples of dimensions of instrument tray 150 of the 5-instrument container 100 are shown in Table 2 below.

TABLE 2

Example dimensions of instrument tray 150 of the 5-instrument container 100

| Dimension | Tolerance (inches) | Specific Example (inches) |
|---|---|---|
| Inside length $L_I$ | +0.125/−0.0 | about 7.249 |
| Inside width $W_I$ | +0.125/−0.0 | about 2.874 |
| Inside height $H_I$ | +0.125/−0.0 | about 0.937 |
| Thickness T | +0.063/−0.0 | about 0.188 |
| Outside length $L_O$ | +0.125/−0.0 | about 7.625 |
| Outside width $W_O$ | +0.125/−0.0 | about 3.250 |
| Outside height $H_O$ | +0.125/−0.0 | about 1.125 |
| Height $H_S$ | +0.063/−0.0 | about 0.750 |
| Diameter D | +0.063/−0.0 | about 0.250 |

Figure 8:
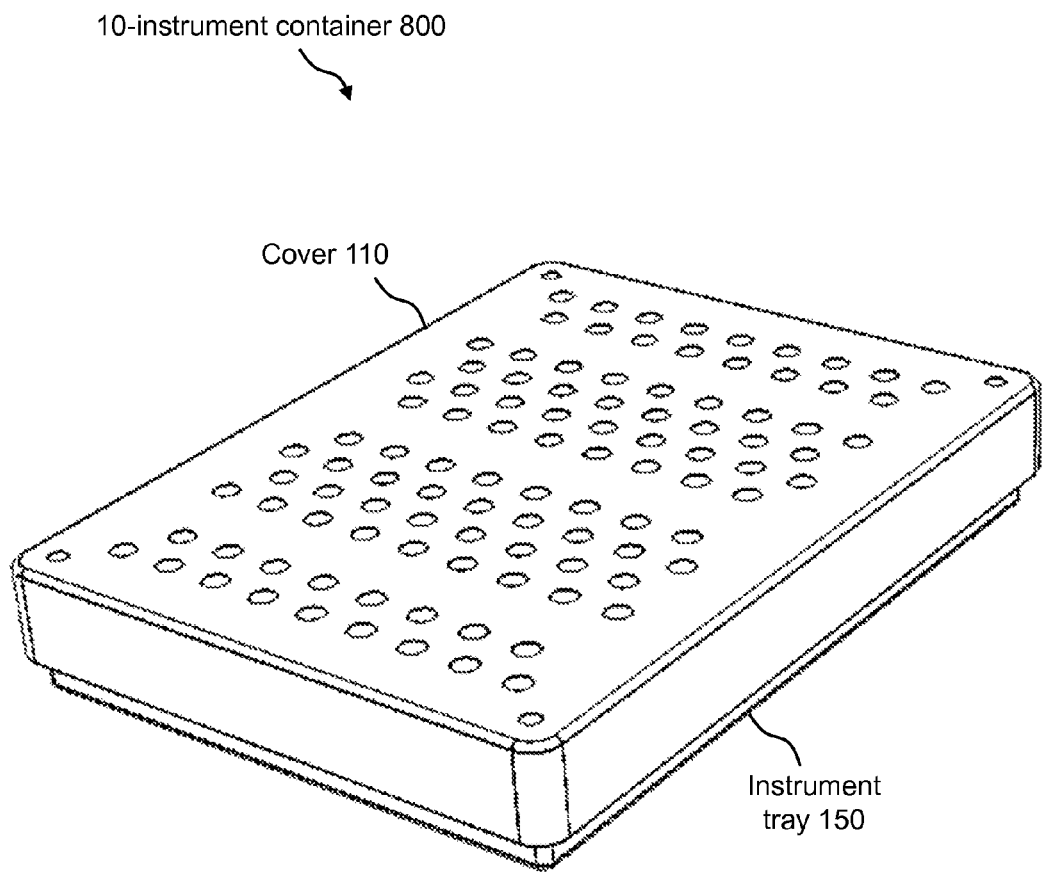
FIG. 8 illustrates a perspective view of a 10-instrument container, which is another example of a flexible container for use in sterilizing, storing, transporting, and presenting medical instruments.

FIG. 8 illustrates a perspective view of a 10-instrument container 800, which is another example of a flexible container for use in sterilizing, storing, transporting, and presenting medical instruments. The 10-instrument container 800 is an example of a flexible container for holding ten instruments, such as ten dental instruments. The 10-instrument container 800 includes cover 110 and instrument tray 150 and is substantially the same as the 5-instrument container 100 described with reference to FIG. 1 through FIG. 7 with respect to its basic features, but differing by dimensions and numbers of features in order to accommodate ten instruments instead of five instruments, as shown with reference to FIG. 8 through FIG. 15.

Figure 9:
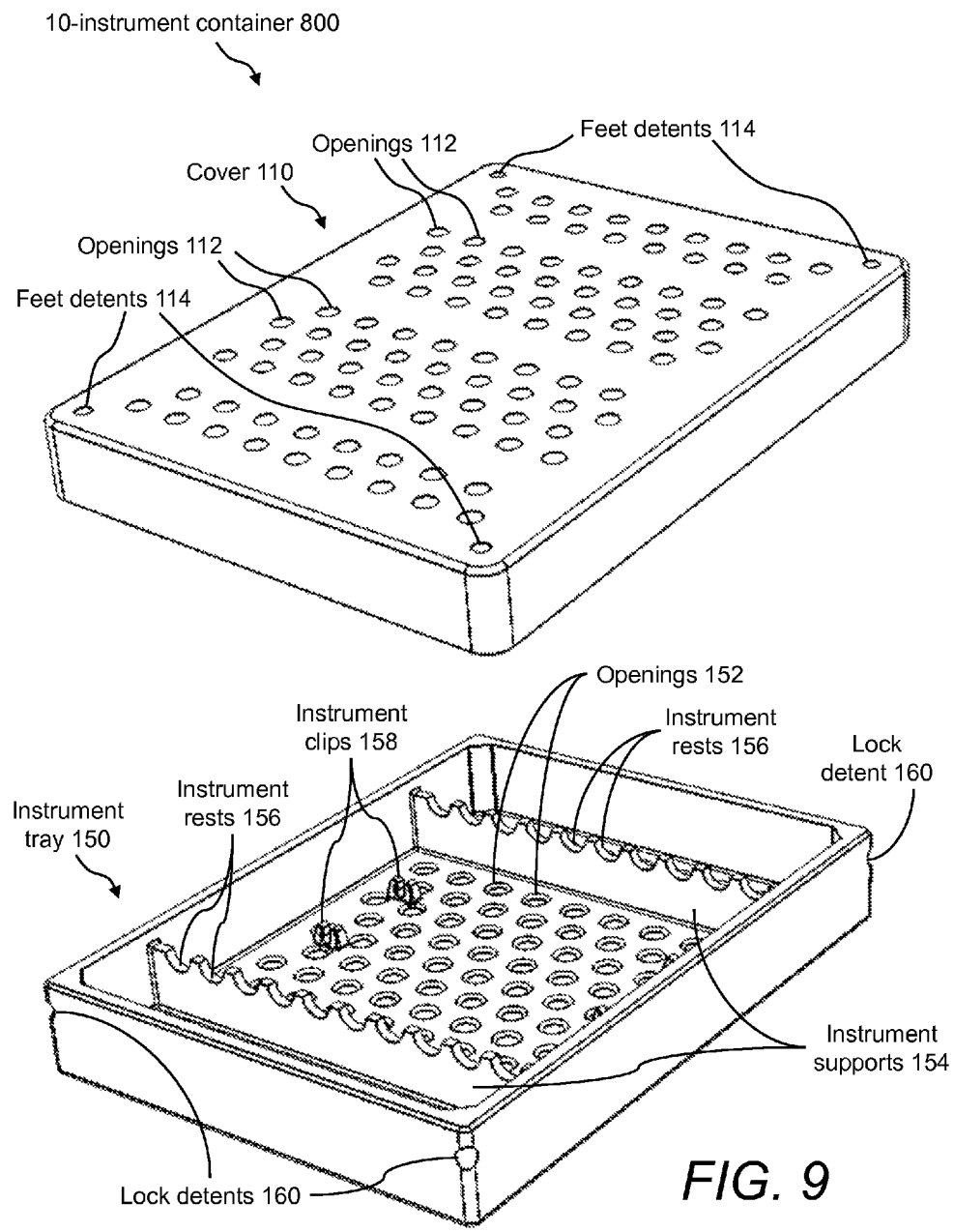
FIG. 9 illustrates a perspective view of a cover and an instrument tray of the 10-instrument container shown in FIG. 8.
Figure 10:
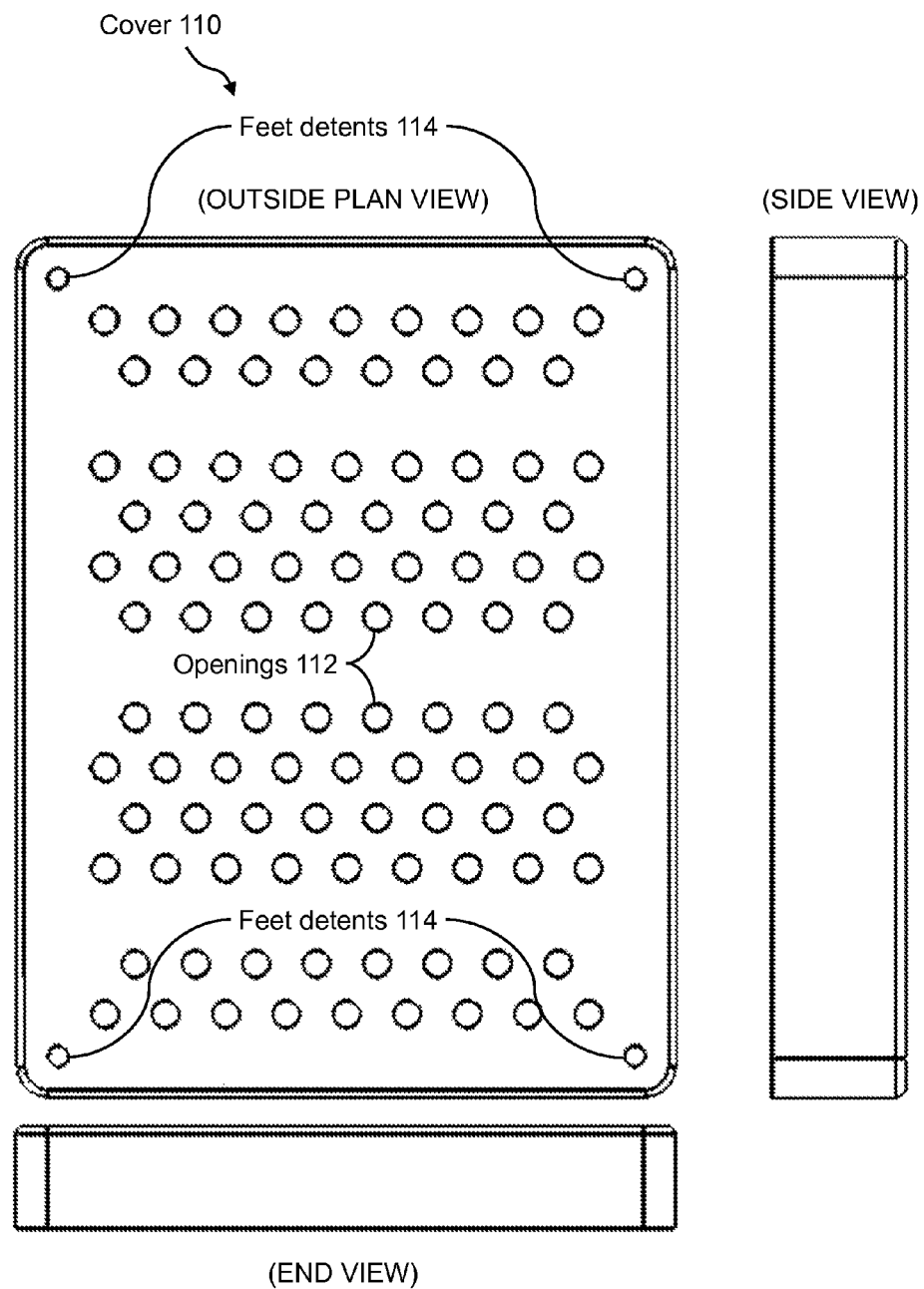
FIG. 10 and FIG. 11 illustrate an outside plan view, an inside plan view, a side view, and an end view of the cover of the 10-instrument container shown in FIG. 8.
Figure 11:
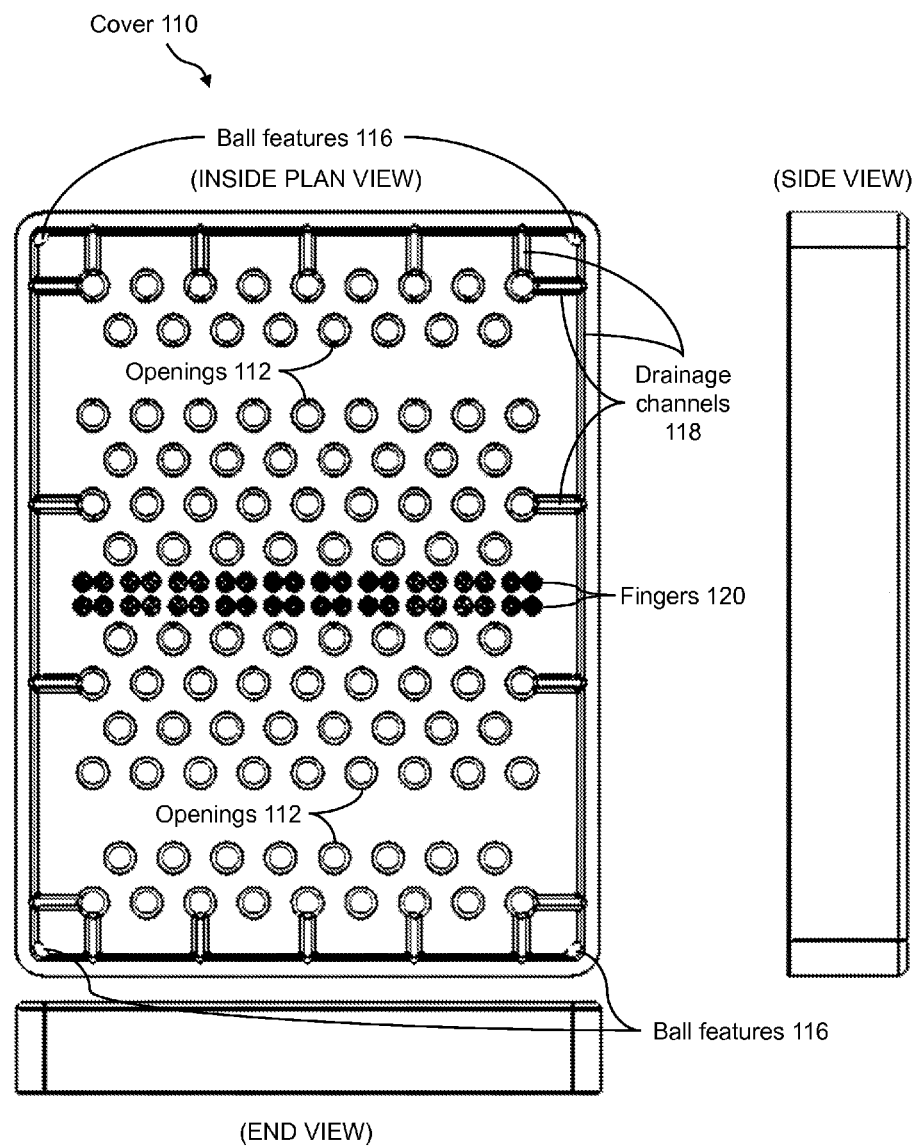
Figure 12:
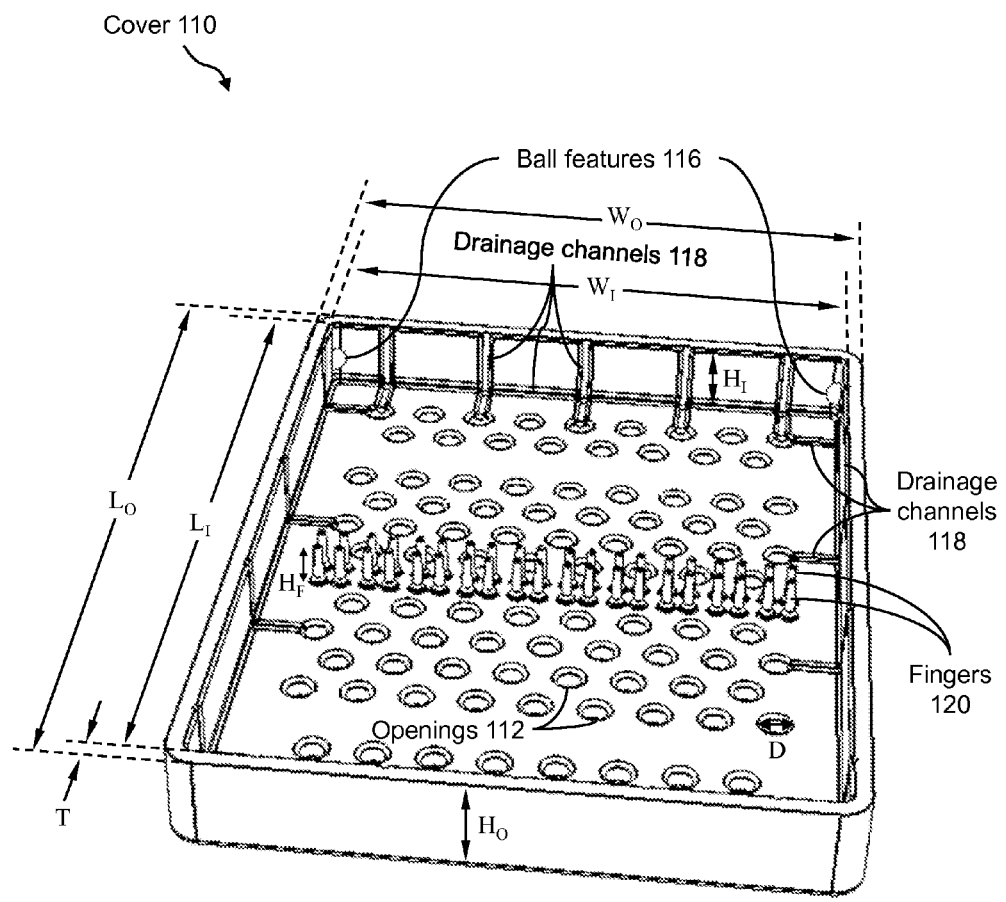
FIG. 12 illustrates a perspective view of the inside of the cover of the 10-instrument container shown in FIG. 8.

FIG. 9 illustrates a perspective view of cover 110 and instrument tray 150 of the 10-instrument container 800 shown in FIG. 8. FIG. 10 and FIG. 11 illustrate an outside plan view, an inside plan view, a side view, and an end view of cover 110 of the 10-instrument container 800 shown in FIG. 8. FIG. 12 illustrates a perspective view of the inside of cover 110 of the 10-instrument container 800 shown in FIG. 8. Cover 110 of the 10-instrument container 800 has certain dimensions, as shown in FIG. 12. Examples of dimensions of cover 110 of the 10-instrument container 800 are shown in Table 3 below.

TABLE 3

Example dimensions of cover 110 of the 10-instrument container 800

| Dimension | Tolerance (inches) | Specific Example (inches) |
| --- | --- | --- |
| Inside length $L_I$ | +0.125/−0.0 | about 7.623 |
| Inside width $W_I$ | +0.125/−0.0 | about 5.749 |
| Inside height $H_I$ | +0.125/−0.0 | about 0.750 |
| Thickness T | +0.063/−0.0 | about 0.188 |
| Outside length $L_O$ | +0.125/−0.0 | about 8.000 |
| Outside width $W_O$ | +0.125/−0.0 | about 6.125 |
| Outside height $H_O$ | +0.125/−0.0 | about 0.938 |
| Height $H_F$ | +0.063/−0.0 | about 0.438 |
| Diameter D | +0.063/−0.0 | about 0.250 |

Figure 13:
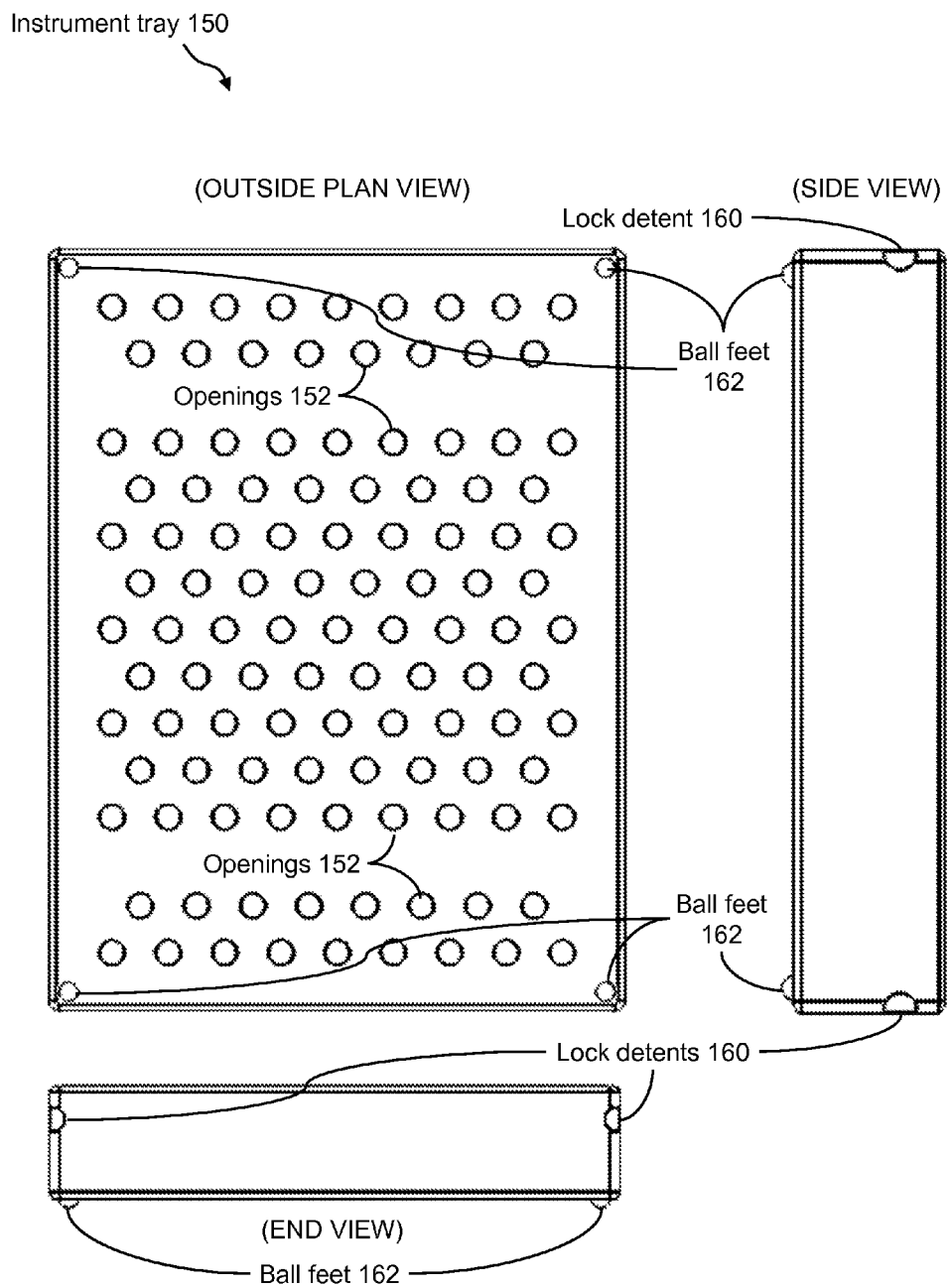
FIG. 13 and FIG. 14 illustrate an outside plan view, an inside plan view, a side view, and an end view of the instrument tray of the 10-instrument container shown in FIG. 8.
Figure 14:
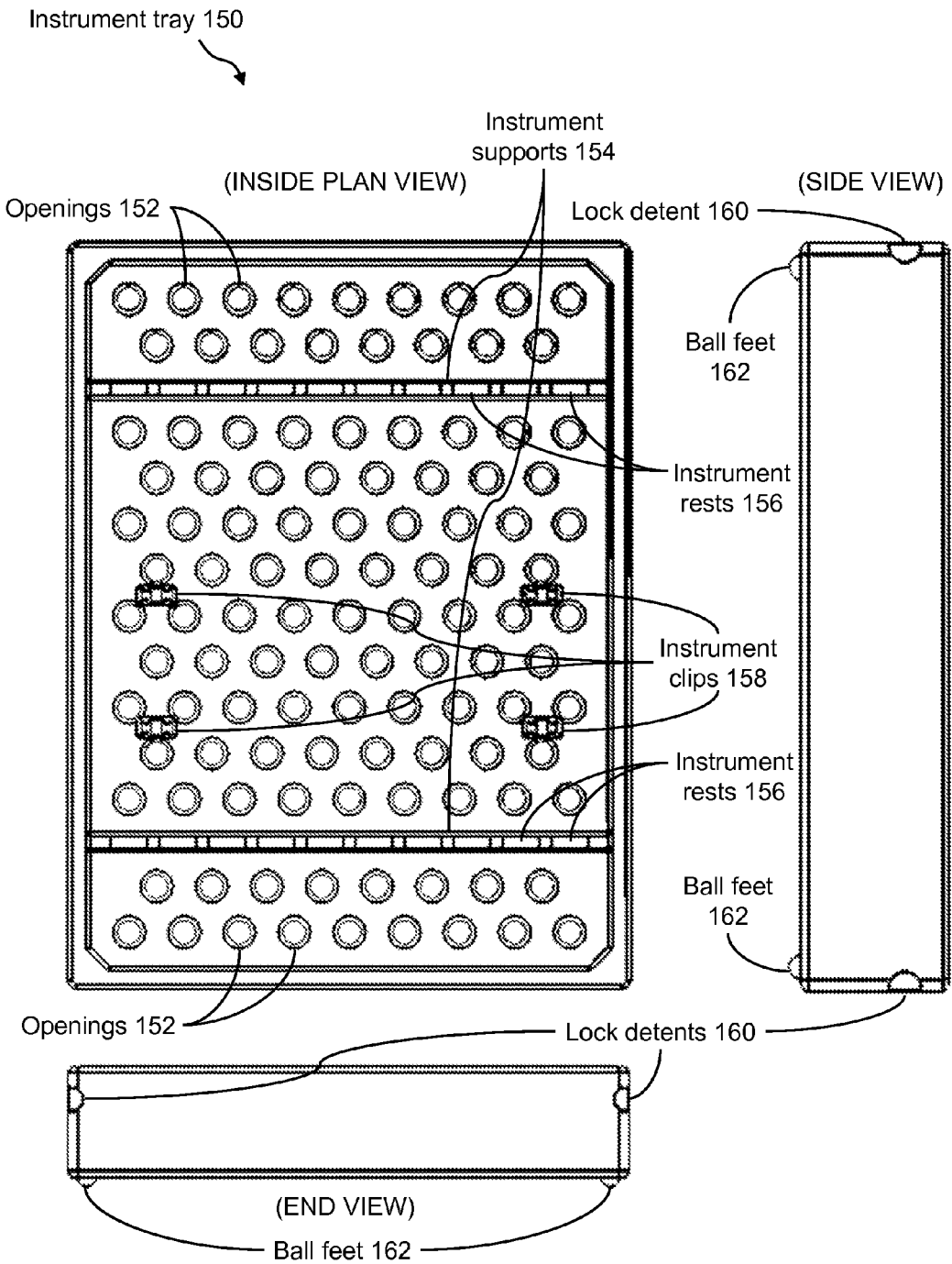
Figure 15:
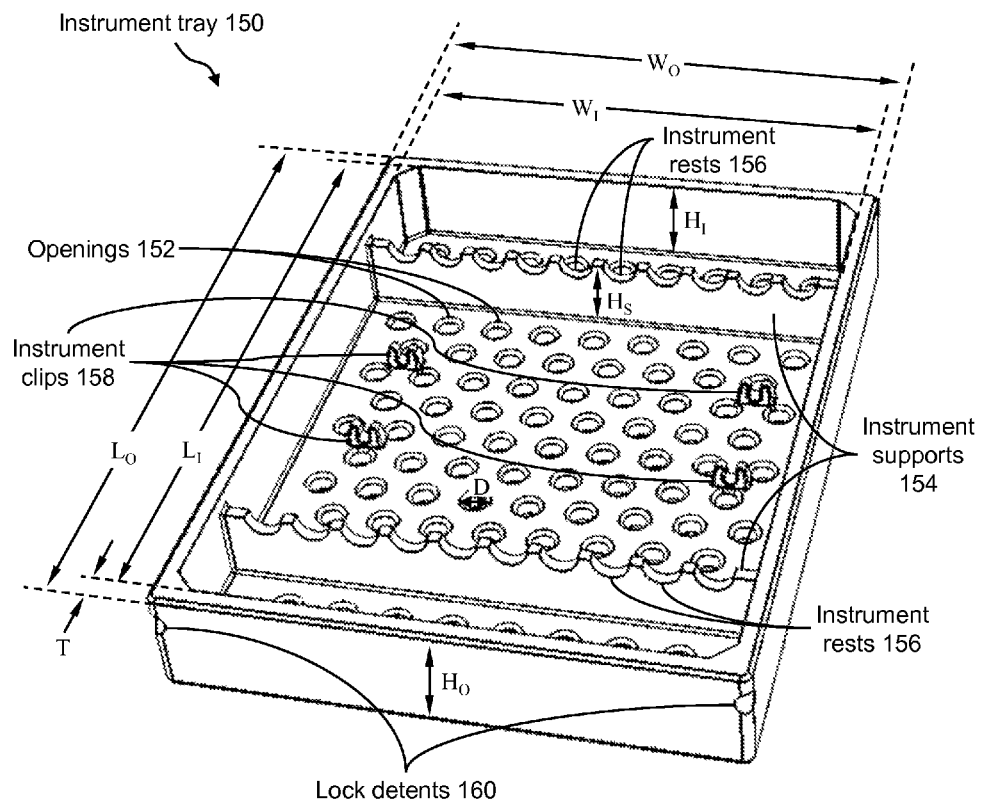
FIG. 15 illustrates a perspective view of the inside of the instrument tray of the 10-instrument container shown in FIG. 8.

FIG. 13 and FIG. 14 illustrate an outside plan view, an inside plan view, a side view, and an end view of instrument tray 150 of the 10-instrument container 800 shown in FIG. 8. FIG. 15 illustrates a perspective view of the inside of instrument tray 150 of the 10-instrument container 800 shown in FIG. 8. In this example, instrument tray 150 includes two sets of instrument clips 158 instead of one set. Instrument tray 150 of the 10-instrument container 800 has certain dimensions, as shown in FIG. 15. Examples of dimensions of instrument tray 150 of the 10-instrument container 800 are shown in Table 4 below.

TABLE 4

Example dimensions of instrument tray 150 of the 10-instrument container 800

| Dimension | Tolerance (inches) | Specific Example (inches) |
| --- | --- | --- |
| Inside length $L_I$ | +0.125/−0.0 | about 7.249 |
| Inside width $W_I$ | +0.125/−0.0 | about 5.374 |
| Inside height $H_I$ | +0.125/−0.0 | about 0.937 |
| Thickness T | +0.063/−0.0 | about 0.188 |
| Outside length $L_O$ | +0.125/−0.0 | about 7.625 |
| Outside width $W_O$ | +0.125/−0.0 | about 5.750 |
| Outside height $H_O$ | +0.125/−0.0 | about 1.125 |
| Height $H_S$ | +0.063/−0.0 | about 0.750 |
| Diameter D | +0.063/−0.0 | about 0.250 |

Figure 16:
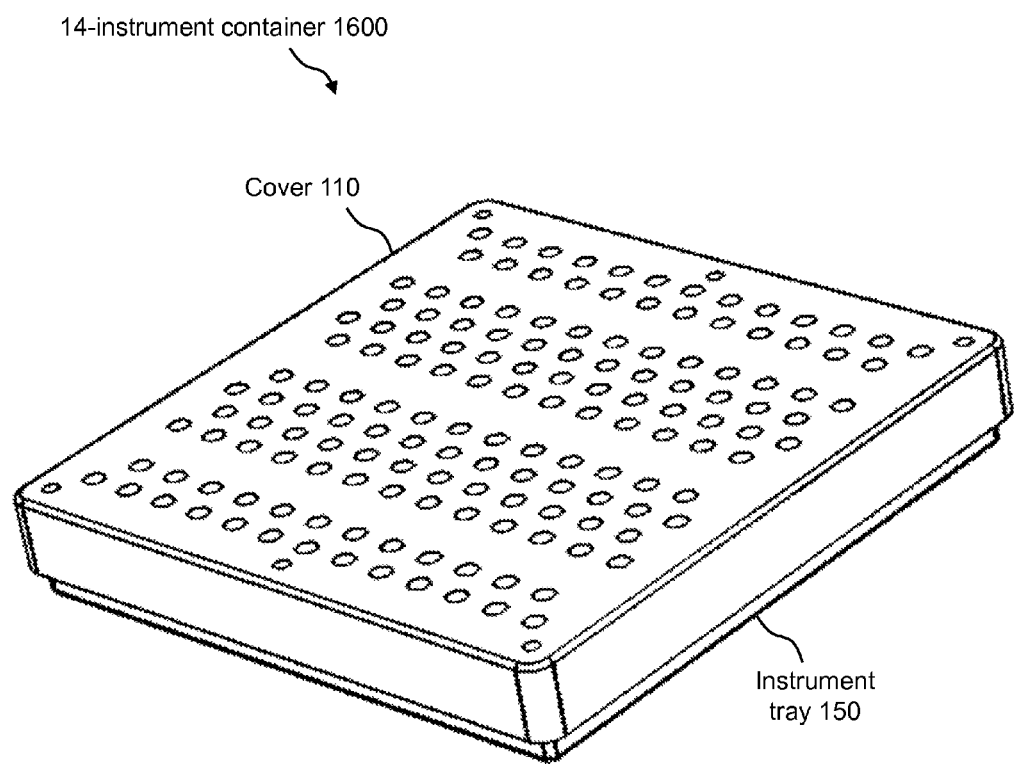
FIG. 16 illustrates a perspective view of a 14-instrument container, which is yet another example of a flexible container for use in sterilizing, storing, transporting, and presenting medical instruments.

FIG. 16 illustrates a perspective view of a 14-instrument container 1600, which is yet another example of a flexible container for use in sterilizing, storing, transporting, and presenting medical instruments. The 14-instrument container 1600 is an example of a flexible container for holding fourteen instruments, such as fourteen dental instruments. The 14-instrument container 1600 includes cover 110 and instrument tray 150 and is substantially the same as the 5-instrument container 100 described with reference to FIG. 1 through FIG. 7 with respect to its basic features, but differing by dimensions and numbers of features in order to accommodate fourteen instruments instead of five instruments, as shown with reference to FIG. 16 through FIG. 23.

Figure 17:
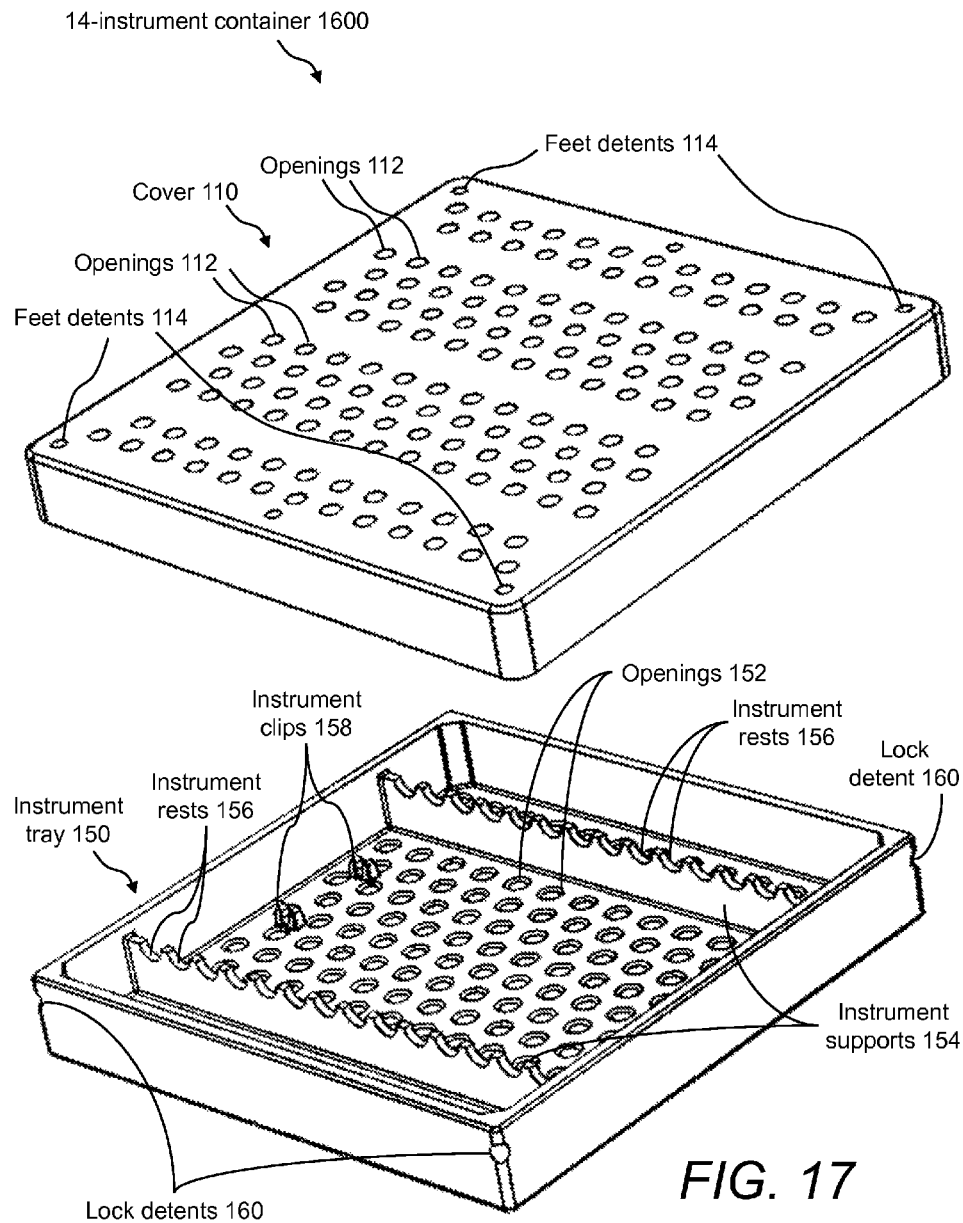
FIG. 17 illustrates a perspective view a the cover and an instrument tray of the 14-instrument container shown in FIG. 16.
Figure 18:
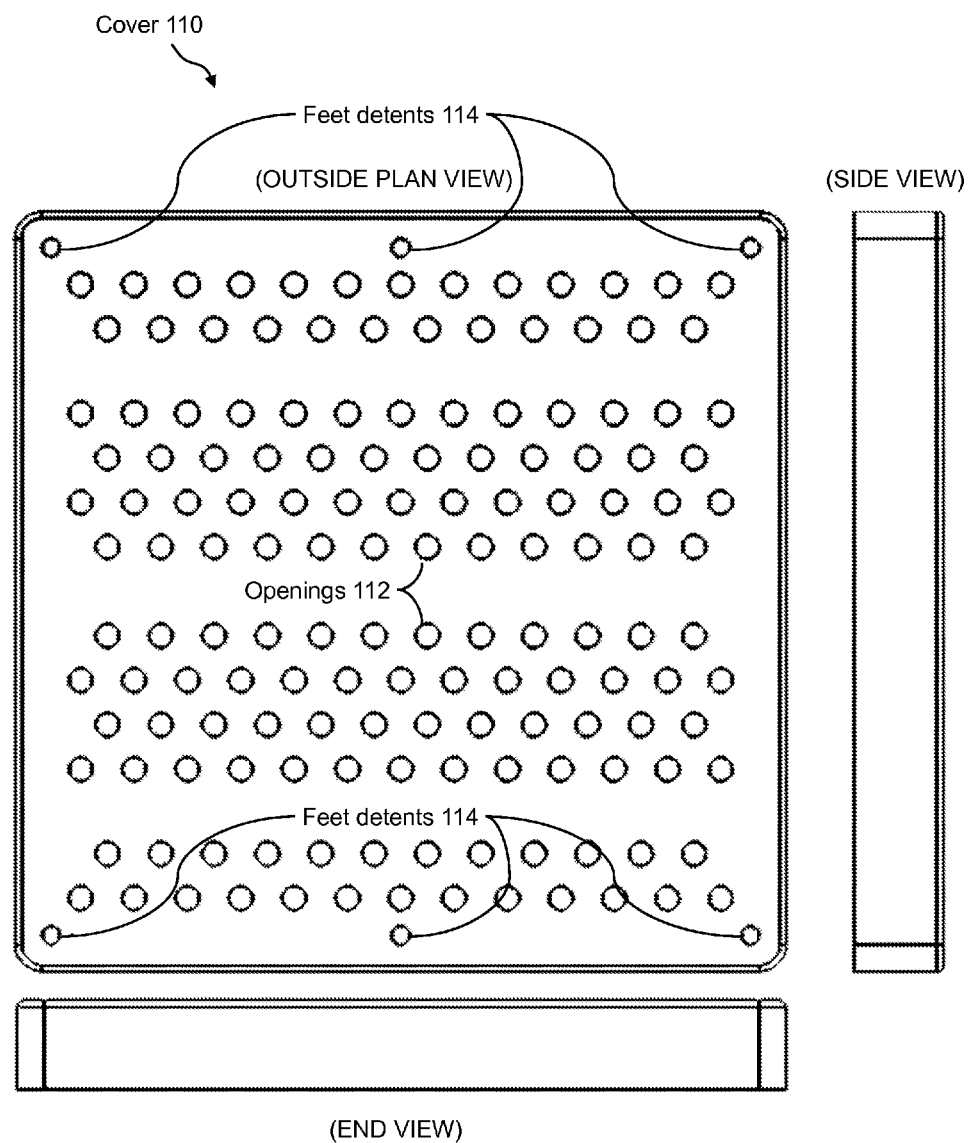
FIG. 18 and FIG. 19 illustrate an outside plan view, an inside plan view, a side view, and an end view of the cover of the 14-instrument container shown in FIG. 16.
Figure 19:
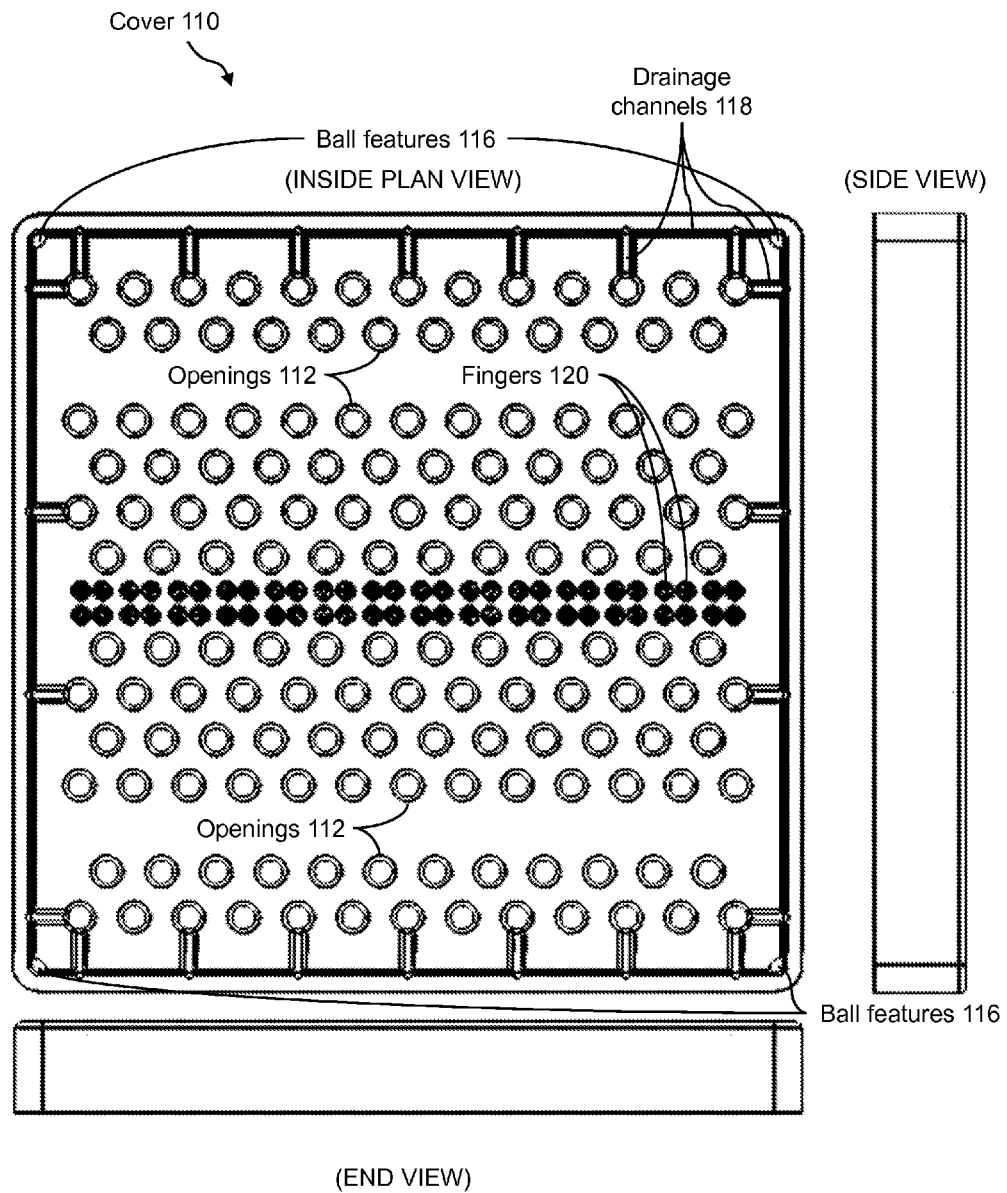
Figure 20:
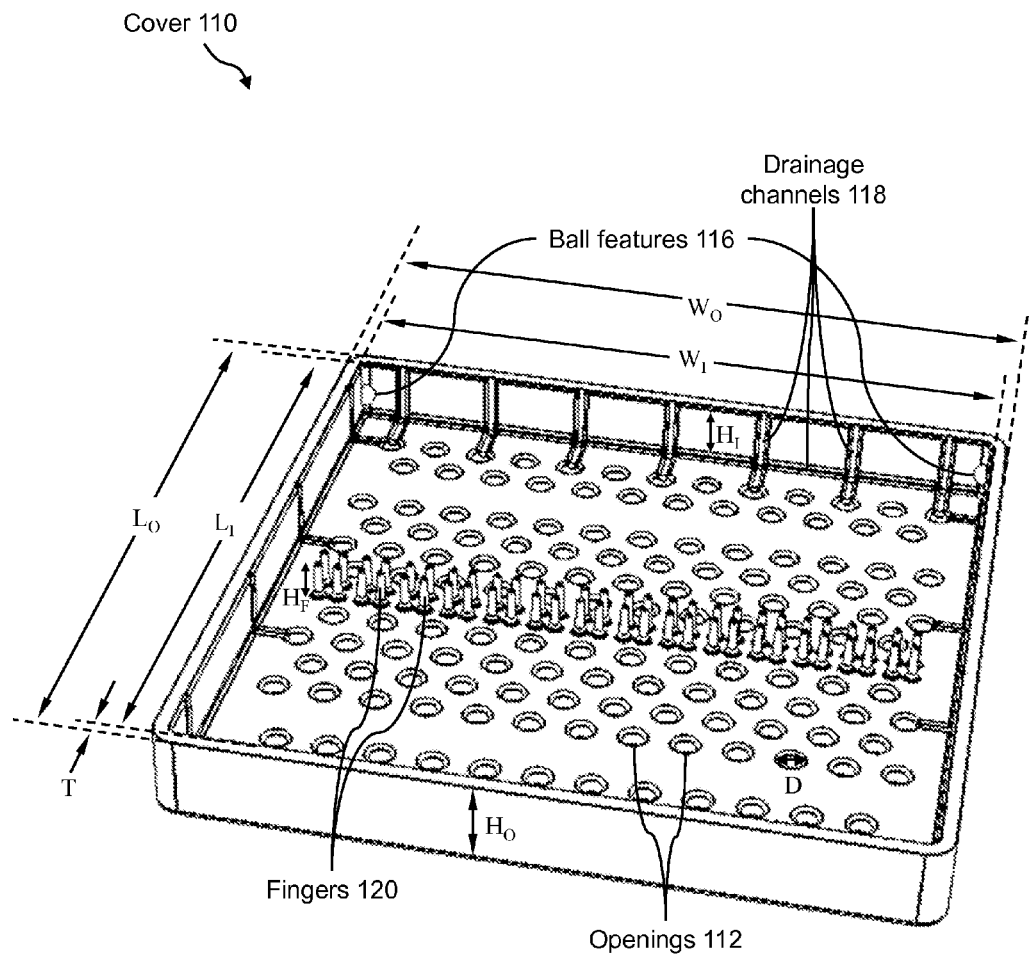
FIG. 20 illustrates a perspective view of the inside of the cover of the 14-instrument container shown in FIG. 16.

FIG. 17 illustrates a perspective view of cover 110 and instrument tray 150 of the 14-instrument container 1600 shown in FIG. 16. FIG. 18 and FIG. 19 illustrate an outside plan view, an inside plan view, a side view, and an end view of cover 110 of the 14-instrument container 1600 shown in FIG. 16. FIG. 20 illustrates a perspective view of the inside of cover 110 of the 14-instrument container 1600 shown in FIG. 16. Cover 110 of the 14-instrument container 1600 has certain dimensions, as shown in FIG. 20. Examples of dimensions of cover 110 of the 14-instrument container 1600 are shown in Table 5 below.

TABLE 5

Example dimensions of cover 110 of the 14-instrument container 1600

| Dimension | Tolerance (inches) | Specific Example (inches) |
| --- | --- | --- |
| Inside length $L_I$ | +0.125/−0.0 | about 7.623 |
| Inside width $W_I$ | +0.125/−0.0 | about 7.749 |
| Inside height $H_I$ | +0.125/−0.0 | about 0.750 |
| Thickness T | +0.063/−0.0 | about 0.188 |
| Outside length $L_O$ | +0.125/−0.0 | about 8.000 |
| Outside width $W_O$ | +0.125/−0.0 | about 8.125 |
| Outside height $H_O$ | +0.125/−0.0 | about 0.938 |
| Height $H_F$ | +0.063/−0.0 | about 0.438 |
| Diameter D | +0.063/−0.0 | about 0.250 |

Figure 21:
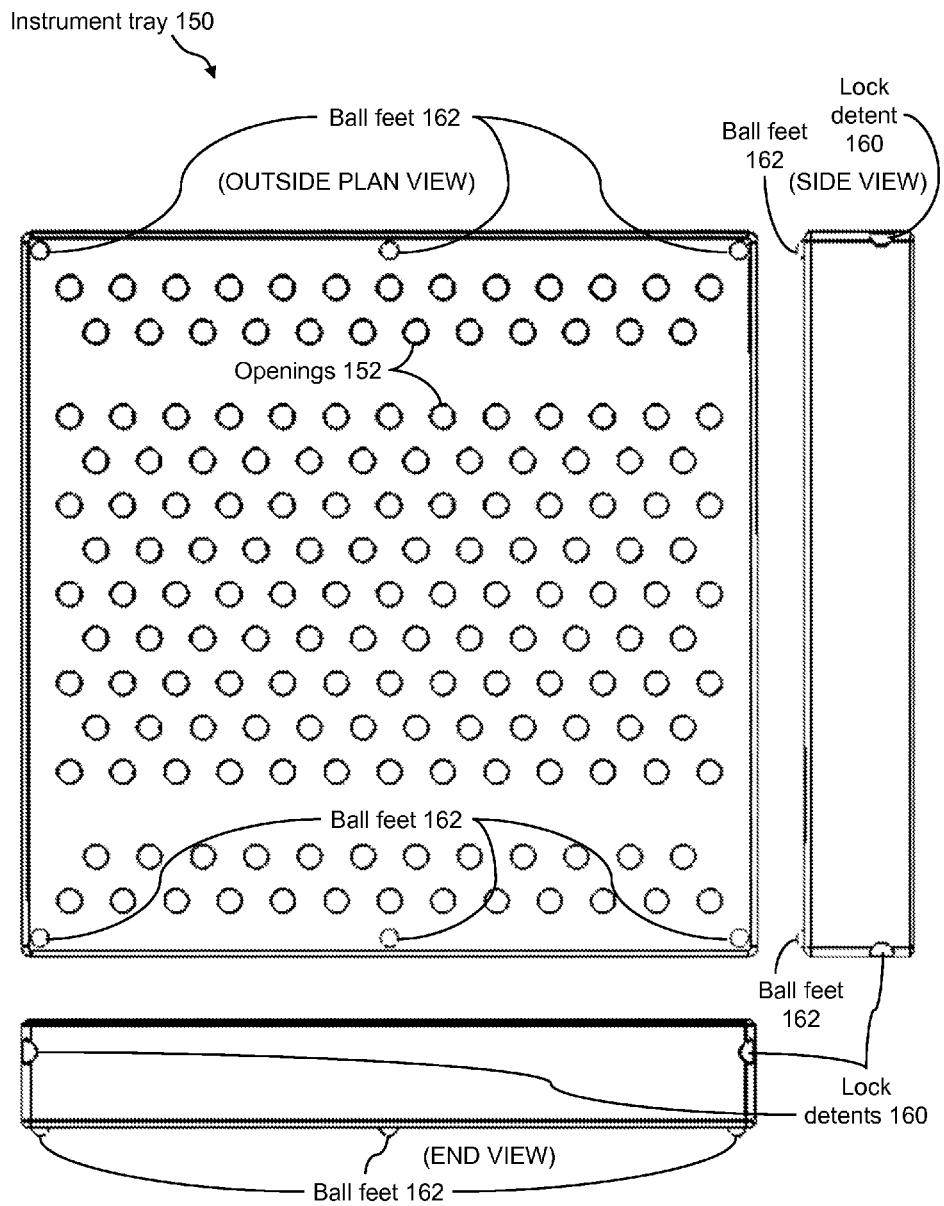
FIG. 21 and FIG. 22 illustrate an outside plan view, an inside plan view, a side view, and an end view of the instrument tray of the 14-instrument container shown in FIG. 16.
Figure 22:
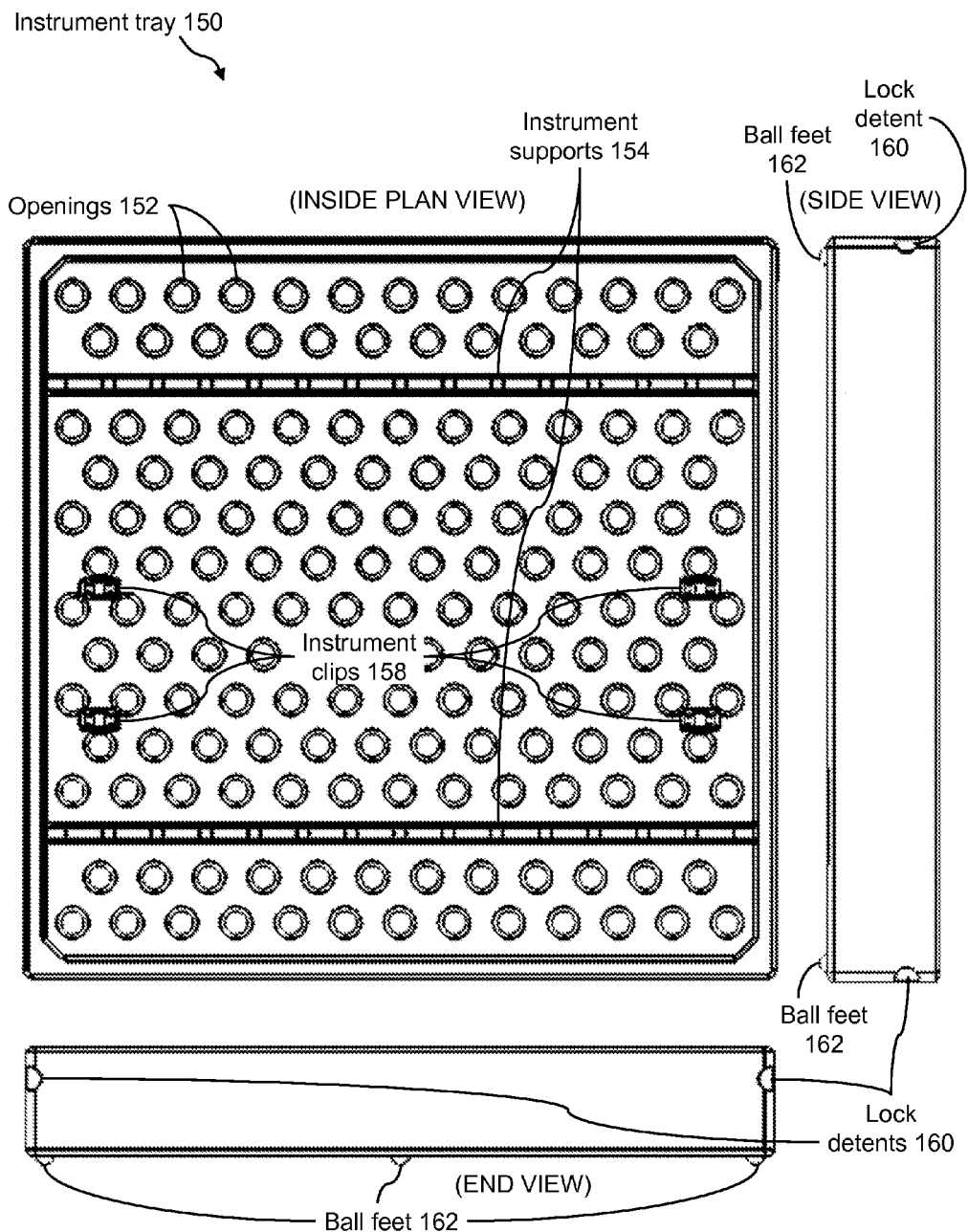
Figure 23:
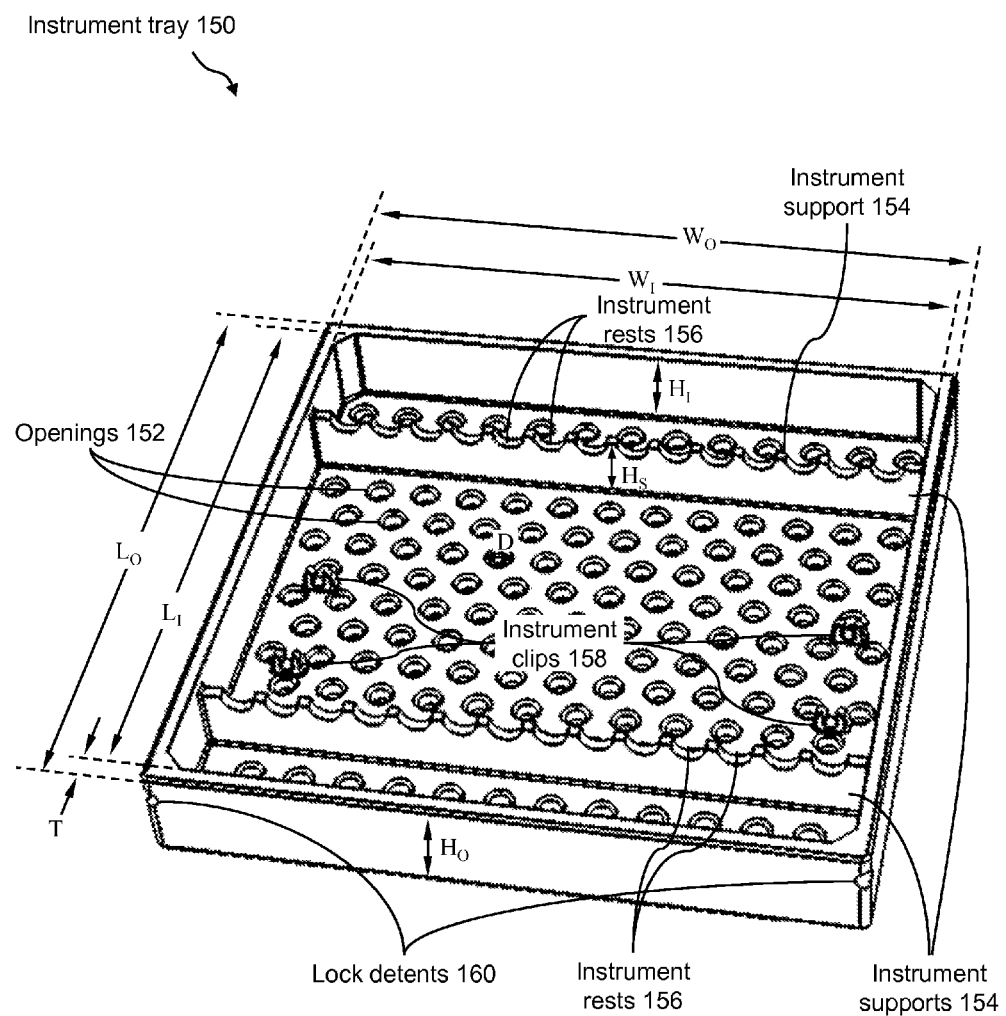
FIG. 23 illustrates a perspective view of the inside of the instrument tray of the 14-instrument container shown in FIG. 16.

FIG. 21 and FIG. 22 illustrate an outside plan view, an inside plan view, a side view, and an end view of instrument tray 150 of the 14-instrument container 1600 shown in FIG. 16. FIG. 23 illustrates a perspective view of the inside of instrument tray 150 of the 14-instrument container 1600 shown in FIG. 16. In this example, instrument tray 150 includes two sets of instrument clips 158 instead of one set. Instrument tray 150 of the 14-instrument container 1600 has certain dimensions, as shown in FIG. 23. Examples of dimensions of instrument tray 150 of the 14-instrument container 1600 are shown in Table 6 below.

TABLE 6

Example dimensions of instrument tray 150 of the 14-instrument container 1600

| Dimension | Tolerance (inches) | Specific Example (inches) |
| --- | --- | --- |
| Inside length $L_I$ | +0.125/−0.0 | about 7.249 |
| Inside width $W_I$ | +0.125/−0.0 | about 7.374 |
| Inside height $H_I$ | +0.125/−0.0 | about 0.937 |
| Thickness T | +0.063/−0.0 | about 0.188 |
| Outside length $L_O$ | +0.125/−0.0 | about 7.625 |
| Outside width $W_O$ | +0.125/−0.0 | about 7.750 |
| Outside height $H_O$ | +0.125/−0.0 | about 1.125 |
| Height $H_S$ | +0.063/−0.0 | about 0.750 |
| Diameter D | +0.063/−0.0 | about 0.250 |

Referring now to FIG. 1 through FIG. 23, while the overall geometries of the 5-instrument container 100, the 10-instrument container 800, and the 14-instrument container 1600 are shown as box-shaped with a rectangular footprint, the footprint of the 5-instrument container 100, the 10-instrument container 800, and the 14-instrument container 1600 is not limited to rectangular. The 5-instrument container 100, the 10-instrument container 800, and the 14-instrument container 1600 can have any footprint, such as square, rectangular, circular, ovular, triangular, hexagonal, octagonal, polygonal, and the like.

Referring again to FIG. 1 through FIG. 23, the flexible containers, such as the 5-instrument container 100 shown in FIG. 1 through FIG. 7, the 10-instrument container 800 shown in FIG. 8 through FIG. 15, and the 14-instrument container 1600 shown in FIG. 16 through FIG. 23, are flexible and elastic in all directions with edges, corners, and surfaces that are soft and pliable. As an example, constructed by injection molding a silicone polymer into a three-dimensional (3D) mold, the semi-rigid silicone containers of this employment can have any number of design features molded into the shape to accomplish instrument retention, air circulation, liquid drainage, closure characteristics, and the like. The flexible containers can be used for instrument storage, instrument organization, chair-side procedures, and instrument decontamination/sterilization processing.

Referring again to FIG. 1 through FIG. 23, an example of the operation of the flexible containers, such as the 5-instrument container 100 shown in FIG. 1 through FIG. 7, the 10-instrument container 800 shown in FIG. 8 through FIG. 15, and the 14-instrument container 1600 shown in FIG. 16 through FIG. 23 can be summarized as follows. The flexible container is opened, meaning that cover 110 is removed from atop instrument tray 150. A sterile air/water syringe tip can be installed in instrument clips 158. Then, sterile instruments, such as sterile surgical or dental instruments, are placed across instrument supports 154 and within instrument rests 156. Then, cover 110 is snap-fitted onto instrument tray 150. Namely, cover 110 is aligned with instrument tray 150 and then pressed onto instrument tray 150 until ball features 116 of cover 110 are snap-fitted into lock detents 160 of instrument tray 150. In so doing, fingers 120 of cover 110 press against the instruments that are in instrument rests 156 of instrument supports 154 of instrument tray 150, thereby retaining the instruments within instrument rests 156. Then, the flexible container, with the instruments therein, can be set aside until ready for use. Optionally, a silicone band (not shown) can be included with the flexible container. The silicone band can be placed, like a rubber band, around the flexible container to further secure its closure.

In use, the flexible container is placed in the workspace of the user (e.g., a medical doctor, medical assistant, dentist, dental assistant, etc). The user opens the flexible container by disengaging cover 110 from instrument tray 150, i.e., by disengaging ball features 116 of cover 110 from lock detents 160 of instrument tray 150. That is, cover 110 is peeled off of instrument tray 150. Cover 110 can be set aside outside of the workspace or cover 110 can be inverted beneath instrument tray 150, with instrument tray 150 resting or "nested" in cover 110. The instruments are used in the medical or dental procedure and then the contaminated instruments are replaced into instrument tray 150. Cover 110 is snap-fitted into instrument tray 150.

The flexible container that is holding the contaminated instruments can be subjected to a sterilization process in which air, sterilization vapors, and/or liquids can be circulated through openings 112 in cover 110 and openings 152 in instrument tray 150. In so doing, the instruments inside the flexible container are exposed to the air, sterilization vapors, and/or liquids and are sterilized and thus readied for reuse.

Referring again to FIG. 1 through FIG. 23, features of instrument tray 150 include, but are not limited to:

(1) Openings 152 to promote the circulation of air, sterilization vapors, and liquids. Openings 152 substantially align with openings 112 in cover 110 so as to maximize flow of these agents. Further, the interior edges of openings 152 are rounded to break surface tension of liquids that may be pooled on the inside surfaces of instrument tray 150, thereby improving drainage;

(2) Instrument rests 156 that hold a number of dental and/or surgical instruments in parallel position and in close proximity to each other;

(3) Customizable instrument rests 156, wherein the silicone construction (as an example) allows instrument rests 156 to be cut with scissors to accommodate large handled instruments;

(4) One or more pairs of flexible instrument clips 158 to securely retain, for example, one or more air/water syringe tips during storage and processing;

(5) Lock detents 160 of a ball-and-detent corner-lock system that receives corresponding ball features 116 in cover 110, wherein the ball-and-detent corner-lock system allows cover 110 to be snap-fitted onto instrument tray 150; and (6) Raised ball feet 162 at the corners that substantially align with corresponding feet detents 114 of cover 110 so as to aid in alignment and stability when stacking multiple flexible containers.

Referring again to FIG. 1 through FIG. 23, features of cover 110 include, but are not limited to:

(1) Openings 112 to promote the circulation of air, sterilization vapors, and liquids. Openings 112 substantially align with openings 152 in instrument tray 150 so as to maximize flow of these agents. Further, the interior edges of openings 112 are rounded to break surface tension of liquids that may be pooled on the inside surfaces of cover 110, thereby improving drainage;

(2) Perimeter drainage channels 118 that create a passageway for liquids to drain rapidly from the interior of the flexible container when the closed container is stored on its side;

(3) Instrument retention fingers 120 that are sized and positioned to bend and flex around variously sized instrument handles so that the fingers 120 retain instruments within instrument rests 156 in instrument tray 150;

(4) Ball features 116 of the ball-and-detent corner-lock system that keeps cover 110 retained upon instrument tray 150 when pressed closed; and (5) Feet detents 114 at the corners that substantially align with the raised ball feet 162 of instrument tray 150 so as to aid in alignment and stability when stacking multiple flexible containers.

Referring again to FIG. 1 through FIG. 23, benefits of the flexible containers disclosed herein, such as the 5-instrument container 100 shown in FIG. 1 through FIG. 7, the 10-instrument container 800 shown in FIG. 8 through FIG. 15, and the 14-instrument container 1600 shown in FIG. 16 through FIG. 23, include, but are not limited to:

(1) A shorter cool down period after heat sterilization as compared with conventional metal instrument containers because the flexible material such as silicone material, dissipates heat faster than, for example, stainless steel or aluminum;

(2) Construction material (e.g., 100% silicone) that can be heated to 375° F. so as to allow for high heat processing. By contrast, most rigid plastics will not reach this temperature without melting;

(3) Smooth and/or rounded edges and corners that pose no risk of tearing latex gloves and/or injuring the user's hands;

(4) Quieter than conventional metal instrument containers because a flexible container eliminates metal-to-metal contact of the container with the metal instruments therein;

(5) A soft, flexible, pliable material (e.g., 100% silicone) that poses no risk of damage to the instruments therein, thereby maximizing the lifetime of the instruments;

(6) A compact footprint that is well-suited for use within a limited workspace; namely, a two-piece design in which, when opened, cover 110 can be completely set aside outside of the workspace or placed or "nested" beneath instrument tray 150, thereby minimizing its overall footprint;

(7) No moving parts that can break or wear out over time, accordingly, the lifetime thereof can be longer than conventional metal instrument containers;

(8) Inexpensive due to inexpensive materials (e.g., silicone) and formed using a simple, well-known manufacturing process (standard injection molding process);

(9) Easy to open, wherein the flexible cover 110 can be easily "peeled" off of instrument tray 150;

(10) More aesthetically pleasing than conventional metal instrument containers because the flexible material can be made of any color;

(11) Because the flexible material can be made of any color, silicone containers can be color-coded for rapid container identification;

(12) Lighter weight than conventional metal instrument containers;

(13) Allows air, sterilization vapors, and/or liquids to enter and exit the interior thereof and come in contact with the surfaces of contaminated instruments, by way of openings 112 and openings 152 and drainage channels 118, so as to promote instrument cleaning and/or sterilization, then instrument drying afterwards; and

(14) As an additional safety feature and built into the design, when cover 110 and instrument tray 150 are together (i.e., when the flexible container is closed) the side-walls and/or end-walls become double thickness and are therefore more resistant to any possibility of a sharp instrument puncturing a side-wall and/or end-wall and becoming a safety hazard during processing.

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicant's invention set forth in this specification, and neither its use nor its absence is intended to limit the scope of the applicant's invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

What is claimed is:

1. A medical instruments container, comprising:
   a. a flexible instrument tray;
   b. a flexible cover, the cover comprising:
      i. a floor;
      ii. two side walls perpendicular to the floor and extending vertically from opposing sides thereof; and
      iii. two end walls perpendicular to the floor and extending vertically from opposing ends thereof;
   c. a plurality of openings formed in the instrument tray and cover; and
   d. drainage channels, including one or more floor drainage channels leading from one or more of the plurality of openings to one or more wall drainage channels formed in one or more of the side walls and/or end walls of the cover, wherein the one or more drainage channels are configured to create a passageway for liquids to drain from an interior of the container when the container is stored on a side thereof.

2. The medical instruments container of claim 1 wherein the flexible material of both the instrument tray and the cover comprises silicone.

3. The medical instruments container of claim 1 wherein one or both of the instrument tray and cover are formed by injection molding.

4. The medical instruments container of claim 1 wherein the plurality of openings formed in the instrument tray substantially aligns with the plurality of openings formed in the cover.

5. The medical instruments container of claim 1 wherein interior edges of the plurality of openings are rounded.

6. The medical instruments container of claim 1 wherein the instrument tray comprises one or more instrument supports.

7. The medical instruments container of claim 6 wherein the one or more instrument supports comprise one or more instrument rests formed thereon.

8. The medical instruments container of claim 7 wherein the one or more instrument rests are configured to support the instruments in a substantially parallel position to one another.

9. The medical instruments container of claim 7 wherein the one or more instrument rests are customizable to support various sized instruments.

10. The medical instruments container of claim 1 wherein the instrument tray comprises one or more pairs of flexible holding clips.

11. The medical instruments container of claim 1 further comprising a locking mechanism configured to secure the cover to the instrument tray.

12. The medical instruments container of claim 11 wherein the locking mechanism comprises a corner-lock mechanism.

13. The medical instruments container of claim 12 wherein the corner-lock mechanism comprises a ball-and-detent, wherein one of the instrument tray and cover comprise detent features or ball features and wherein the other of the one of the instrument tray and cover comprise corresponding ball features or detent features respectively.

14. The medical instruments container of claim 13 wherein the detent features are configured to receive corresponding ball features, wherein the ball-and-detent configuration allows the cover to be snap-fitted onto the instrument tray.

15. The medical instruments container of claim 1 wherein the instrument tray comprises raised feet that substantially align with corresponding detents on the cover so as to aid in alignment and stability when stacking multiple containers.

16. The medical instruments container of claim 1 wherein the instrument tray comprises detents that substantially align with corresponding raised features on the cover so as to aid in alignment and stability when stacking multiple containers.

17. The medical instruments container of claim 1 wherein the plurality of instrument retention fingers are flexible and configured to substantially retain instruments within an instrument rest in of the instrument tray.

* * * * *